(12) United States Patent
Chen et al.

(10) Patent No.: US 11,932,692 B2
(45) Date of Patent: Mar. 19, 2024

(54) METHODS OF TREATING CANCER PAIN BY ADMINISTERING A PD-1 INHIBITOR

(71) Applicants: Regeneron Pharmaceuticals, Inc., Tarrytown, NY (US); Sanofi Biotechnology, Paris (FR)

(72) Inventors: Chieh-I Chen, Brooklyn, NY (US); Medha R. Sasane, Bridgewater, NJ (US); Denise P. Bury-Maynard, Bridgewater, NJ (US)

(73) Assignees: Regeneron Pharmaceuticals, Inc., Tarrytown, NY (US); Sanofi Biotechnology, Paris (FR)

(*) Notice: Subject to any disclaimer, the term of this patent is extended or adjusted under 35 U.S.C. 154(b) by 15 days.

(21) Appl. No.: 17/464,819

(22) Filed: Sep. 2, 2021

(65) Prior Publication Data

US 2022/0064304 A1 Mar. 3, 2022

Related U.S. Application Data

(60) Provisional application No. 63/186,375, filed on May 10, 2021, provisional application No. 63/161,519, filed on Mar. 16, 2021, provisional application No. 63/074,282, filed on Sep. 3, 2020.

(30) Foreign Application Priority Data

Jul. 29, 2021 (EP) .................................... 21315132

(51) Int. Cl.
*C07K 16/28* (2006.01)
*A61K 39/395* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *A61K 2039/505* (2013.01); *C07K 2317/565* (2013.01)

(58) Field of Classification Search
None
See application file for complete search history.

(56) References Cited

U.S. PATENT DOCUMENTS

| | | |
|---|---|---|
| 6,808,710 B1 | 10/2004 | Wood et al. |
| 7,488,802 B2 | 2/2009 | Collins et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,246,995 B2 | 8/2012 | Dai et al. |
| 8,257,740 B1 | 9/2012 | Sung et al. |
| 8,354,509 B2 | 1/2013 | Carven et al. |
| 8,609,089 B2 | 12/2013 | Langermann et al. |
| 8,686,119 B2 | 4/2014 | Rotem-Yehudar et al. |
| 8,779,105 B2 | 7/2014 | Korman et al. |
| 8,900,587 B2 | 12/2014 | Carven et al. |
| 9,402,899 B2 | 8/2016 | Honjo et al. |
| 9,624,298 B2 | 4/2017 | Nastri et al. |
| 9,938,345 B2 | 4/2018 | Papadopoulos et al. |
| 9,987,500 B2 | 6/2018 | Papadopoulos et al. |
| 10,011,656 B2 | 7/2018 | Freeman et al. |
| 2013/0247234 A1 | 9/2013 | McWhirter et al. |
| 2017/0044259 A1 | 2/2017 | Tipton et al. |
| 2017/0290808 A1 | 10/2017 | Charo et al. |
| 2017/0327567 A1* | 11/2017 | Skokos ............... A61N 5/06 |
| 2019/0040137 A1 | 2/2019 | Hu et al. |

FOREIGN PATENT DOCUMENTS

| | | |
|---|---|---|
| EP | 1591527 A1 | 11/2005 |
| EP | 3177649 A1 | 6/2017 |
| JP | 2006340714 A | 12/2006 |
| WO | 2004056875 A1 | 7/2004 |
| WO | 2006121168 A1 | 11/2006 |
| WO | 2007005874 A2 | 1/2007 |
| WO | 2009030285 A1 | 3/2009 |
| WO | 2009114335 A2 | 9/2009 |
| WO | 2010077634 A1 | 7/2010 |
| WO | 2011110621 A1 | 9/2011 |
| WO | 2011159877 A2 | 12/2011 |
| WO | 2013181452 A1 | 12/2013 |
| WO | 2013181634 A2 | 12/2013 |

(Continued)

OTHER PUBLICATIONS

Migden et al (NEJM, 2018, 379:341-351).*
Goto et al (Current Treatment Options in Oncology, 2019, 20:34, pp. 1-10).*
Wang et al (Journal of Cancer Institute, Jul. 2020; 130:3603-3620).*
Graff et al (Annals of Oncology, 2016, 27(Supplement 6):vi243-vi265).*
Migden et al 2020 (JCO, May 20, 2020; 38, No. 15_suppl; abstract 10033).*
Aaronson et al., "The European Organization for Research and Treatment of Cancer QLQ-C30: a quality-of-life instrument for use in international clinical trials in oncology", J Natl Cancer Inst, (1993) 85(5):365-376.

(Continued)

*Primary Examiner* — Laura B Goddard
(74) *Attorney, Agent, or Firm* — Fox Rothschild LLP; Aparna G. Patankar

(57) ABSTRACT

The present disclosure provides methods of treating or inhibiting cancer pain in a patient in need thereof, including selecting a patient with cancer, and administering to the patient a therapeutically effective amount of a programmed death 1 (PD-1) inhibitor. The present disclosure also provides methods of reducing analgesic use in a patient in need thereof, including selecting a patient with cancer, and administering to the patient a therapeutically effective amount of a PD-1 inhibitor, wherein the patient is being treated with background analgesic therapy prior to administration of the PD-1 inhibitor. In some embodiments, the disclosed methods concurrently lead to tumor regression, pain reduction, and reduced use of analgesic therapy.

45 Claims, 18 Drawing Sheets

Specification includes a Sequence Listing.

(56) References Cited

FOREIGN PATENT DOCUMENTS

| WO | 2016149201 A2 | 9/2016 | | |
|---|---|---|---|---|
| WO | 2017034916 A1 | 3/2017 | | |
| WO | 2018209329 A1 | 11/2018 | | |
| WO | WO-2018209329 A1 | * 11/2018 | ........... | A61B 5/4824 |
| WO | 2019200229 A1 | 10/2019 | | |
| WO | 2020154189 A1 | 7/2020 | | |

OTHER PUBLICATIONS

Ahmed et al., "Cemiplimab-rwlc as first and only treatment for advanced cutaneous squamous cell carcinoma", Expert Rev Clin Pharmacol, (2019) 12(10):947-951.

Arruebo et al., "Antibody-conjugated nanoparticles for biomedical applications," J. Nanomat., (2009) vol. 2009, Article ID 439389 (24 pp.).

Arunachalam et al., "Quality of Life in Cancer Patients with Disfigurement due to Cancer and its Treatments", Indian J Palliat Care, (2011) 17(3):184-90.

Atherton et al., "Using the Skindex-16 and Common Terminology Criteria for Adverse Events to assess rash symptoms: results of a pooled-analysis (N0993)", Support Care Cancer, (2012) 20(8):1729-35.

Benyamin et al., "Opioid complications and side effects", Pain Physician, (2008) 11(2 Supp):S105-S120.

Bottomley et al., "Health related quality of life outcomes in cancer clinical trials", Eur J Cancer, (2005) 41(12):1697-709.

Brook et al., "Late side effects of radiation treatment for head and neck cancer", Radiat Oncol J., (2020) 38(2):84-92.

Burova et al., "Characterization of the Anti-PD-1 Antibody REGN2810 and Its Antitumor Activity in Human PD-1 Knock-In Mice", Mol Cancer Ther, (2017) 16(5):861-70.

Chren et al., "Measurement properties of Skindex-16: a brief quality-of-life measure for patients with skin diseases", J Cutan Med Surg., (2001) 5(2):105-110.

Cowey et al., "Clinical outcomes among unresectable, locally advanced, and metastatic cutaneous squamous cell carcinoma patients treated with systemic therapy", Cancer Med, (2020) 9(20):7381-87.

Cranmer et al., "Treatment of Unresectable and Metastatic Cutaneous Squamous Cell Carcinoma", Oncologist, (2010) 15(12):1320-28.

Eisenhauser et al., "New response evaluation criteria in solid tumours: revised RECIST guideline (version 1.1)", Eur J Cancer, (2009) 45(2):228-247.

Gerring et al., "Orbital exenteration for advanced periorbital non-melanoma skin cancer: prognostic factors and survival", Eye (Lond), (2017) 31(3):379-88.

Grob et al., "Pembrolizumab Monotherapy for Recurrent or Metastatic Cutaneous Squamous Cell Carcinoma: A Single-Arm Phase II Trial (KEYNOTE-629)", J Clin Oncol, (2020) 38(25):2916-25.

Gorelik et al., "Preclinical characterization of a novel fully human IgG1 anti-PD-L1 mAb CK-301", American Association for Cancer Research Annual Meeting (AACR), (2016) Abstract 4606.

Haefeli et al., "Pain assessment", Eur Spine J, (2006) 15 Suppl (Suppl 1): S17-S24.

Hagg et al., "The clinical importance of changes in outcome scores after treatment for chronic low back pain", Eur Spine J, (2003) 12(1):12-20.

Hansson et al., "Assessment of quality of life using Skindex-16 in patients with advanced basal cell carcinoma treated with vismodegib in the STEVIE study", Eur J Dermatol, (2018) 28(6):775-83.

Jensen et al., "The measurement of clinical pain intensity: a comparison of six methods", Pain, (1986) 27(1):117-126.

Katz et al., "Psychosocial adjustment in head and neck cancer: the impact of disfigurement, gender and social support", Head Neck, (2003) 25(2):103-12.

Karia et al., "Evaluation of American Joint Committee on Cancer, International Union Against Cancer, and Brigham and Women's Hospital tumor staging for cutaneous squamous cell carcinoma", J Clin Oncol, (2014) 32(4):327-34.

Kondo et al., "Health-related quality of life after surgical removal of an eye", Ophthalmic Plast Reconstr Surg, (2013) 29(1):51-6.

Langer, "New methods of drug delivery", Science, (1990) 249(4976):1527-1533.

LIBTAYO® [cemiplimab-rwlc] injection full US prescribing information, Regeneron Pharmaceuticals, Inc. and Sanofi-Aventis US LLC (Mar. 2020).

Mannion et al., "Pain measurement in patients with low back pain", Nat Clin Pract Rheumatol, (2007) 3(11):610-618.

Maubec et al., "Phase II Study of Pembrolizumab As First-Line, Single-Drug Therapy for Patients With Unresectable Cutaneous Squamous Cell Carcinomas", J Clin Oncol, (2020) 38(26):3051-61.

McLeod et al., "Interpreting patient-reported outcome results: US Fda guidance and emerging methods", Expert Rev Pharmacoecon Outcomes Res, (2011) 11(2):163-169.

Migden et al., "Emerging trends in the treatment of advanced basal cell carcinoma", Cancer Treat Rev, (2018) 64:1-10.

Migden et al., "PD-1 Blockade with Cemiplimab in Advanced Cutaneous Squamous-Cell Carcinoma", N Engl J Med, (2018) 379(4):341-351.

Migden et al., "Primary analysis of phase 2 results of cemiplimab, a human monoclonal anti-PD-1, in patients (pts) with locally advanced cutaneous squamous cell carcinoma (laCSCC)", J Clin Oncol, (2019) 37(15 suppl):6015.

Migden et al., "Cemiplimab in locally advanced cutaneous squamous cell carcinoma: results from an open-label, phase 2, single-arm trial", Lancet Oncol, (2020) 21(2):294-305.

Migden et al., "Health-related quality of life (HRQL) in patients with advanced cutaneous squamous cell carcinoma (CSCC) treated with cemiplimab: Post hoc exploratory analyses of a phase II clinical trial", J Clin Oncol, (2020) 38(15 suppl):10033.

Mills et al., "Itch and Pain in Nonmelanoma Skin Cancer: Pain as an Important Feature of Cutaneous Squamous Cell Carcinoma", Arch Dermatol, (2012) 148(12):1422-1423.

National Institute for Health and Care Excellence, "Cemiplimab for treating metastatic or locally advanced cutaneous squamous cell carcinoma" (2019) available at [https://www.nice.org.uk/guidance/gid-ta10304/documents/final-appraisal-determination-document].

Ogon et al., "Chronic low back pain measurement with visual analogue scales in different settings", Pain, (1996) 64(3):425-428.

Osoba et al., "Interpreting the significance of changes in health-related quality-of-life scores", J Clin Oncol, (1998) 16(1):139-144.

Powell et al., "Compendium of excipients for parenteral formulations" PDA, J Pharm Sci Technol, (1998) 52(5):238-311.

Que et al., "Cutaneous squamous cell carcinoma", J Am Acad Dermatol, (2018) 78:237-47.

Revicki et al., "Recommended methods for determining responsiveness and minimally important differences for patient-reported outcomes", J Clin Epidemiol, (2008) 61(2):102-109.

Rhee et al., "Creation of a quality of life instrument for nonmelanoma skin cancer patients", Laryngoscope, (2005) 115(7):1178-85.

Rischin et al., "1318P—Phase II study of 2 dosing regimens of cemiplimab, a human monoclonal anti-PD-1, in metastatic cutaneous squamous cell carcinoma (mCSCC)", Ann Oncol, (2019) 30(suppl 5):v536-v537.

Rischin et al., "Phase 2 study of cemiplimab in patients with metastatic cutaneous squamous cell carcinoma: primary analysis of fixed-dosing, long-term outcome of weight-based dosing", J Immunother Cancer, (2020) 8:e000775 (8 pp.).

Schmults et al., "Factors Predictive of Recurrence and Death From Cutaneous Squamous Cell Carcinoma", JAMA Dermatol, (2013) 149(5):541-47.

Scott et al., "EORTC QLQ-C30 Reference Values Manual", EORTC Quality of Life Group, Brussels, Belgium (2008) 2nd ed.

Steenrod et al., "A Qualitative Comparison of Symptoms and Impact of Varying Stages of Basal Cell Carcinoma", Dermatol Ther (Heidelb), (2015) 5(3):183-199.

Stratigos et al., "Diagnosis and treatment of invasive aquamous cell carcinoma of the skin: European consensus- based interdisciplinary guideline", Eur J Cancer (2015) 51(14):1989-2007.

(56) References Cited

OTHER PUBLICATIONS

Stratigos et al., "European interdisciplinary guideline on invasive squamous cell carcinoma of the skin: Part 2. Treatment", Eur J Cancer, (2020) 128:60-82.

Stratigos et al., "LBA47 Primary analysis of phase II results for cemiplimab in patients (pts) with locally advanced basal cell carcinoma (laBCC) who progress on or are intolerant to hedgehog inhibitors (HHIs)", Ann Oncol, (2020) 31 (suppl 4):S1175-1176.

Taylor et al., "A transgenic mouse that expresses a diveristy of human sequence heavy and light chain Immunoglobulins", Nucl Acids Res, (1992) 20(23):6287-6295.

Keir et al., "Programmed Death-1 (PD-1): PD-Ligand 1 Interactions Inhibit TCR-Mediated Positive Selection of Thymocytes"; J of Immunology; (2005) 175(11):7372-7379.

Riella et al., "Role of the PD-1 Pathway in the Immune Response"; Am J of Transplantation, (2012), 12(10):2575-2587.

Da Silva, "Anti-PD-1 monoclonal antibody Cancer immunotheraphy"; Drugs of the future; (2014), 39(1):15-24.

Brahmer et al., "Phase I Study of Single-Agent Anti-Programmed Death-1 (MDX-1106) in Refractory Solid Tumors: Safety, Clinical Activity, Pharmacodynamics, and Immunologic Correlates" J of Clin Oncol, (2010), 28(9): 3167-3175.

Zoran et al., "Programmed death 1 (PD-1) lymphocytes and ligand (PD-L1) in colorectal cancer and their relationship to microsatellite instability status"; J Clin Oncol; 32(5s)(abstr 3625), 2 pgs (May 30, 2014), available at http://meetinglibrary.asco.org/content/133958-144.

McDermott et al., "PD-1 as a potential target in cancer therapy" Cancer Med., 2(5):662-673 (2013).

Tsai et al., "PD-1 and PD-L1 Antibodies for Melonama", Human Vaccines & Immunotherapeutics (2014) 10: 3111-3116.

Momtaz et al., "Immunoligic Checkpoints in Cancer Therapy: Focus on the Programmed Death-I (PD-I) Receptor Pathway", Pharmacogenomics and Personalized Medicine (2014) 7: 357-365.

Von Korff et al., "Assessing global pain severity by self-report in clinical and health services research", Spine, (2000) 25(24):3140-51.

Wang et al., "Treatment-Related Adverse Events of PD-1 and PD-L1 Inhibitors in Clinical Trials: A Systematic Review and Meta-analysis", JAMA Oncol, (2019) 5(7):1008-19.

Weinberg et al., "Metastatic cutaneous squamous cell carcinoma: an update", Dermatol Surg, (2007) 33(8):885-99.

Wu et al., "Receptor-mediated in vitro gene transformation by a soluble DNA carrier system", J Biol Chem, (1987) 262(10):4429-4432.

Yet et al., "Evidence-based investment selection: Prioritizing agricultural development investments under climatic and socio-political risk using Bayesian networks", PloS One, (2015) 15(7):e0136460-e (22 pp.).

Zanoli et al., "Lessons learned searching for a HRQoL instrument to assess the results of treatment in persons with umbar disorders", Spine (Phila Pa 1976), (2000) 25(24):3178-85.

Zhang et al., "Structural basis of a novel PD-L1 nanobody for immune checkpoint blockade", Cell Discovery, (2017) 3:170004 (12 pages).

International Search Report and Wirtten Opinion dated Jan. 7, 2022 for PCT/US2021/048785 (21 pages).

Wang et al., "PD-1 blockade inbidits osteoclast formation and murine bone cancer pain", J Clin Invest. (2020), 130(7):3603-3620.

Wang et al., "Tumor Cell-intrinsic PD-1 receptor is a tumor suppressor and mediates resistance to PD-1 blockade therapy", PNAS (2020), 117(12):6640-6650.

Garcia et al., "Tolerability and antitumor activity of cemiplimab, a human monocolonal anti-PD-1, in patients with non-small cell lung cancer (NSCLC): Interim data from phase 1 dose escalation and NSCLC Expansion Cohort", J of Clin Oncol (2018), 36(Supp 15):e21057.

Kitano et al., "Phase I study of cemiplimab, a human monoclonal anitbody to programmed death (PD)-1, in Japanese patients (pts) with advanced malignancies: Results from the dose exploration", J Clin Oncol (2019), 37(Supp 8):33.

Wang et al., "Anti-PD-1 treatment impairs opioid antinociception in rodents and nonhuman primates", Sci Trans Med (2020), 12:eaaw6471.

National Comprehensive Cancer Network. National Comprehensive Cancer Network Clinical practice guidelines in oncology: squamous cell skin cancer (Version 2.2020) (2020), 52 pp, at [https://www.nccn.org/professionals/physician_gls/pdf/squamous.pdf].

* cited by examiner

METHODS OF TREATING CANCER PAIN BY ADMINISTERING A PD-1 INHIBITOR

CROSS-REFERENCE TO RELATED APPLICATIONS

This application claims the benefit of priority to U.S. Provisional Patent Application No. 63/074,282 filed Sep. 3, 2020, U.S. Provisional Patent Application No. 63/161,519 filed Mar. 16, 2021, U.S. Provisional Patent Application No. 63/186,375 filed May 10, 2021, and European Patent Application No. 21315132.7 filed Jul. 29, 2021, the disclosures of all of which are hereby incorporated by reference herein in their entireties.

The present application contains a Sequence Listing that was submitted electronically to the USPTO in ASCII text file format (text file name FINAL US Seq Listing-10849US01; 179227.02301; 6.39 kilobytes; created on Sep. 1, 2021) and is hereby incorporated by reference.

FIELD

The present disclosure generally relates to methods of treating or inhibiting cancer pain in a patient in need thereof, including selecting a patient with cancer and administering to the patient a therapeutically effective amount of a programmed death 1 (PD-1) inhibitor. The present disclosure also relates to methods of reducing opioid use in a patient in need thereof, including selecting a patient with cancer, wherein the patient is being treated with analgesic therapy, and administering to the patient a therapeutically effective amount of a PD-1 inhibitor.

BACKGROUND

Pain is an important symptom in the management of cancers from both patient and clinician perspectives. Cancer pain, which can be caused by the disease itself or by treatments, is very common in people with cancer. Many cancer patients experience pain while undergoing treatment, and almost all patients experience pain in the advanced stages of cancer. Cancer pain may depend on many different factors, such as the stage of the disease and a patient's tolerance for pain. Cancer pain can originate from the primary cancer itself or from other areas in the body where the cancer has spread (metastases). As a tumor grows, it may put pressure on nerves, bones or other organs, causing pain. Pain may also result from fracturing of bones, infection or inflammation associated with the disease. Cancer pain may not just arise from the physical effect of the cancer on a region of the body, but also may be caused by the chemicals that may be secreted from cancerous cells and/or tissues. The type of cancer pain may vary as well, including, for example, acute, chronic, or breakthrough pain. Cancer pain may also vary in the duration of each pain episode, its severity and its frequency of occurrence.

Cancer pain is commonly treated with analgesics, such as opioids (e.g., fentanyl, oxycodone, hydrocodone, codeine, morphine), non-steroidal anti-inflammatory drugs (NSAIDs), acetaminophen, and the like. Opioids are known to cause side effects, such as sedation, dizziness, nausea, vomiting, constipation, physical dependence, tolerance and respiratory depression. Additionally, long term negative consequences of opioids may include psychological addiction and abuse (Benyamin et al., 2008, *Pain Physician*, 11:S105-S120). Thus, repeated use of opioids for relief of cancer pain can lead to opiate abuse, tolerance, and dependence, among other risks and unwanted side effects. Accordingly, there is a need for safe and effective therapies for treating or inhibiting cancer pain in patients with cancer, and for reducing analgesic use (e.g., opioid use) in the treatment of such pain.

SUMMARY

In one aspect, the disclosed technology relates to a method of treating or inhibiting cancer pain, including: (a) selecting a patient with cancer; and (b) administering to the patient a therapeutically effective amount of a programmed death 1 (PD-1) inhibitor. In some embodiments, the cancer is selected from anal cancer, bladder cancer, bone cancer, breast cancer, brain cancer, cervical cancer, colon cancer, colorectal cancer, endometrial cancer, esophageal cancer, head and neck cancer, kidney cancer, liver cancer, lung cancer, myeloma, ovarian cancer, pancreatic cancer, prostate cancer, salivary gland cancer, skin cancer, stomach cancer, testicular cancer, and uterine cancer. In some embodiments, the cancer is skin cancer. In some embodiments, the skin cancer is a non-melanoma skin cancer. In some embodiments, the skin cancer is cutaneous squamous cell carcinoma (CSCC) or basal cell carcinoma (BCC). In some embodiments, the CSCC is metastatic CSCC or unresectable locally advanced CSCC. In some embodiments, the BCC is locally advanced BCC (laBCC) or metastatic BCC. In some embodiments, the BCC has progressed on, or the BCC patient was intolerant to, hedgehog inhibitor (HHI) therapy. In some embodiments, functioning and quality of life of the patient is improved or maintained from baseline, as measured by EORTC QLQ-C30 and SKINDEX-16. In some embodiments, the patient is receiving analgesic therapy as a background medication prior to administration of the PD-1 inhibitor. In some embodiments, the analgesic therapy is selected from an opioid, a non-steroid anti-inflammatory drug (NSAID), a steroid, acetaminophen, and combinations thereof. In some embodiments, the analgesic therapy includes an opioid.

In some embodiments of the disclosed methods of treating or inhibiting cancer pain, the administration of the PD-1 inhibitor leads to reduced use of analgesic therapy by the patient. In some embodiments, the method further includes reducing the amount of the analgesic therapy received by the patient by 20% or more within 1 year after administration of the PD-1 inhibitor. In some embodiments, the pain is reduced by about 20% or more within 1 year after administration of the PD-1 inhibitor. In some embodiments, the administration of the PD-1 inhibitor concurrently leads to reduced cancer pain and at least 30% decrease in tumor cells or tumor size. In some embodiments, the administration of the PD-1 inhibitor concurrently leads to reduced analgesic use and at least 30% decrease in tumor cells or tumor size. In some embodiments, the administration of the PD-1 inhibitor concurrently leads to reduced opioid use and at least 30% decrease in tumor cells or tumor size. In some embodiments, the administration of the PD-1 inhibitor reduces pain, reduces the need for analgesic therapy, promotes tumor regression, reduces tumor cell load, reduces tumor burden, prevents tumor recurrence in the patient, and/or increases patient survival.

In some embodiments of the disclosed methods of treating or inhibiting cancer pain, the PD-1 inhibitor is administered in combination with a second therapeutic agent or therapy selected from an analgesic, a non-steroid anti-inflammatory drug (NSAID), radiation, surgery, a cancer vaccine, imiquimod, an anti-viral agent, photodynamic therapy, HHI therapy, a PD-L1 inhibitor, a LAG3 inhibitor, a CTLA-4 inhibitor, a GITR agonist, a TIM3 inhibitor, a BTLA inhibitor, a TIGIT inhibitor, a CD38 inhibitor, a CD47 inhibitor, an IDO inhibitor, a CD28 activator, a VEGF antagonist, an Ang2 inhibitor, a TGFβ inhibitor, an EGFR inhibitor, an antibody to a tumor-specific antigen, a cancer vaccine, a GM-CSF, an oncolytic virus, a cytotoxin, a chemotherapeutic agent, an IL-6R inhibitor, an IL-4R inhibitor, an IL-10 inhibitor, a cytokine, an antibody drug conjugate, an anti-inflammatory drug, and a dietary supplement.

In some embodiments of the disclosed methods of treating or inhibiting cancer pain, the PD-1 inhibitor is selected from an anti-PD-1 antibody or antigen-binding fragment thereof, an anti-PD-L1 antibody or antigen-binding fragment thereof, and an anti-PD-L2 antibody or antigen-binding fragment thereof. In some embodiments, the PD-1 inhibitor is an anti-PD-1 antibody or antigen-binding fragment thereof.

In some embodiments of the disclosed methods of treating or inhibiting cancer pain, the PD-1 inhibitor is an anti-PD-1 antibody or antigen-binding fragment thereof that includes a heavy chain variable region (HCVR) including three heavy chain complementarity determining regions (CDRs) (HCDR1, HCDR2 and HCDR3) and a light chain variable region (LCVR) including three light chain CDRs (LCDR1, LCDR2 and LCDR3), wherein: HCDR1 has an amino acid sequence of SEQ ID NO: 3; HCDR2 has an amino acid sequence of SEQ ID NO: 4; HCDR3 has an amino acid sequence of SEQ ID NO: 5; LCDR1 has an amino acid sequence of SEQ ID NO: 6; LCDR2 has an amino acid sequence of SEQ ID NO: 7; and LCDR3 has an amino acid sequence of SEQ ID NO: 8. In some embodiments, the HCVR includes an amino acid sequence of SEQ ID NO: 1. In some embodiments, the LCVR includes an amino acid sequence of SEQ ID NO: 2. In some embodiments, the anti-PD-1 antibody or antigen-binding fragment thereof includes an HCVR/LCVR amino acid sequence pair of SEQ ID NOs: 1/2. In some embodiments, the anti-PD-1 antibody or antigen-binding fragment thereof includes a heavy chain and a light chain, wherein the heavy chain has an amino acid sequence of SEQ ID NO: 9. In some embodiments, the anti-PD-1 antibody includes a heavy chain and a light chain, wherein the light chain has an amino acid sequence of SEQ ID NO: 10. In some embodiments, the anti-PD-1 antibody includes a heavy chain and a light chain, wherein the heavy chain has an amino acid sequence of SEQ ID NO: 9 and the light chain has an amino acid sequence of SEQ ID NO: 10.

In some embodiments of the disclosed methods of treating or inhibiting cancer pain, the PD-1 inhibitor is an anti-PD-1 antibody or antigen-binding fragment thereof including a HCVR with 90%, 95%, 97% or 98% sequence identity to SEQ ID NO: 1. In some embodiments, the PD-1 inhibitor is an anti-PD-1 antibody or antigen-binding fragment thereof including a LCVR with 90%, 95%, 97% or 98% sequence identity to SEQ ID NO: 2. In some embodiments, the PD-1 inhibitor is an anti-PD-1 antibody or antigen-binding fragment thereof including a HCVR with 90%, 95%, 97% or 98% sequence identity to SEQ ID NO: 1, and a LCVR with 90%, 95%, 97% or 98% sequence identity to SEQ ID NO: 2.

In some embodiments of the disclosed methods of treating or inhibiting cancer pain, the PD-1 inhibitor is cemiplimab or a bioequivalent thereof. In some embodiments, the PD-1 inhibitor is an anti-PD-1 antibody selected from the group consisting of cemiplimab, nivolumab, pembrolizumab, pidilizumab, MED10608, BI 754091, PF-06801591, spartalizumab, camrelizumab, JNJ-63723283, and MCLA-134.

In some embodiments, the PD-1 inhibitor is an anti-PD-L1 antibody selected from the group consisting of REGN3504, avelumab, atezolizumab, durvalumab, MDX-1105, LY3300054, FAZ053, STI-1014, CX-072, KN035, and CK-301.

In some embodiments of the disclosed methods of treating or inhibiting cancer pain, the PD-1 inhibitor is administered at a dose of 5 mg to 1500 mg. In some embodiments, the PD-1 inhibitor is administered at a dose of 200 mg, 250 mg, 350 mg, 600 mg, 700 mg, or 1050 mg. In some embodiments, the PD-1 inhibitor is administered at a dose of 1 mg/kg to 20 mg/kg of the patient's body weight. In some embodiments, the PD-1 inhibitor is administered at a dose of 1 mg/kg, 3 mg/kg or 10 mg/kg of the patient's body weight. In some embodiments, the PD-1 inhibitor is administered as one or more doses, wherein each dose is administered two weeks, three weeks, four weeks, five weeks or six weeks after the immediately preceding dose. In some embodiments, the PD-1 inhibitor is administered intravenously, subcutaneously, or intraperitoneally.

In another aspect, the disclosed technology relates to a kit including a programmed death 1 (PD-1) inhibitor in combination with written instructions for use of a therapeutically effective amount of the PD-1 inhibitor for treating or inhibiting cancer pain in a patient with cancer. In some embodiments, the kit further includes instructions for use of a therapeutically effective amount of the PD-1 inhibitor for treating or inhibiting the growth of a tumor. In some embodiments, the cancer is selected from anal cancer, bladder cancer, bone cancer, breast cancer, brain cancer, cervical cancer, colon cancer, colorectal cancer, endometrial cancer, esophageal cancer, head and neck cancer, kidney cancer, liver cancer, lung cancer, myeloma, ovarian cancer, pancreatic cancer, prostate cancer, salivary gland cancer, skin cancer, stomach cancer, testicular cancer, and uterine cancer.

In another aspect the disclosed technology relates to a method of reducing use of analgesic therapy by a cancer patient, including: (a) selecting a patient with cancer; and (b) administering to the patient a therapeutically effective amount of a programmed death 1 (PD-1) inhibitor, wherein the patient is receiving analgesic therapy as a background medication prior to the administration of the PD-1 inhibitor. In some embodiments, the cancer is selected from anal cancer, bladder cancer, bone cancer, breast cancer, brain cancer, cervical cancer, colon cancer, colorectal cancer, endometrial cancer, esophageal cancer, head and neck cancer, kidney cancer, liver cancer, lung cancer, myeloma, ovarian cancer, pancreatic cancer, prostate cancer, salivary gland cancer, skin cancer, stomach cancer, testicular cancer, and uterine cancer. In some embodiments, the cancer is skin cancer. In some embodiments, the cancer is metastatic cutaneous squamous cell carcinoma (CSCC) or unresectable locally advanced CSCC.

In some embodiments of the disclosed methods of reducing use of analgesic therapy by a cancer patient, the analgesic therapy is selected from an opioid, a non-steroid anti-inflammatory drug (NSAID), a steroid, acetaminophen, and combinations thereof. In some embodiments, the analgesic therapy includes an opioid. In some embodiments, the amount of analgesic therapy received by the patient is reduced by at least 20% within 1 year after administration of the PD-1 inhibitor as compared to the amount of analgesic therapy received by the patient before administration of the PD-1 inhibitor. In some embodiments, the administration of the PD-1 inhibitor concurrently leads to reduced analgesic use and at least 30% decrease in tumor cells or tumor size. In some embodiments, the administration of the PD-1 inhibitor concurrently leads to reduced opioid use and at least 30% decrease in tumor cells or tumor size. In some embodiments, the administration of the PD-1 inhibitor concurrently leads to reduced cancer pain and at least 30% decrease in tumor cells or tumor size. In some embodiments, the administration of the PD-1 inhibitor concurrently leads to reduced cancer pain, reduced opioid use and a tumor response selected from the group consisting of stable disease (SD), partial response (PR) and complete response (CR), as determined using RECIST criteria.

In some embodiments of the disclosed methods of reducing use of analgesic therapy by a cancer patient, the PD-1 inhibitor is administered in combination with a second therapeutic agent or therapy selected from an analgesic, a non-steroid anti-inflammatory drug (NSAID), radiation, surgery, a cancer vaccine, imiquimod, an anti-viral agent, photodynamic therapy, HHI therapy, a PD-L1 inhibitor, a LAG3 inhibitor, a CTLA-4 inhibitor, a GITR agonist, a TIM3 inhibitor, a BTLA inhibitor, a TIGIT inhibitor, a CD40 inhibitor, a CD47 inhibitor, an IDO inhibitor, a CD28 activator, a VEGF antagonist, an Ang2 inhibitor, a TGFβ inhibitor, an EGFR inhibitor, an antibody to a tumor-specific antigen, a cancer vaccine, a GM-CSF, an oncolytic virus, a cytotoxin, a chemotherapeutic agent, an IL-6R inhibitor, an IL-4R inhibitor, an IL-10 inhibitor, a cytokine, an antibody drug conjugate, an anti-inflammatory drug, and a dietary supplement.

In some embodiments of the disclosed methods of reducing use of analgesic therapy by a cancer patient, the PD-1 inhibitor is selected from an anti-PD-1 antibody or antigen-binding fragment thereof, an anti-PD-L1 antibody or antigen-binding fragment thereof, and an anti-PD-L2 antibody or antigen-binding fragment thereof. In some embodiments, the PD-1 inhibitor is an anti-PD-1 antibody or antigen-binding fragment thereof. In some embodiments, the PD-1 inhibitor is an anti-PD-1 antibody or antigen-binding fragment thereof that includes a heavy chain variable region (HCVR) including three heavy chain complementarity determining regions (CDRs) (HCDR1, HCDR2 and HCDR3) and a light chain variable region (LCVR) including three light chain CDRs (LCDR1, LCDR2 and LCDR3), wherein: HCDR1 has an amino acid sequence of SEQ ID NO: 3; HCDR2 has an amino acid sequence of SEQ ID NO: 4; HCDR3 has an amino acid sequence of SEQ ID NO: 5; LCDR1 has an amino acid sequence of SEQ ID NO: 6; LCDR2 has an amino acid sequence of SEQ ID NO: 7; and LCDR3 has an amino acid sequence of SEQ ID NO: 8.

In some embodiments of the disclosed methods of reducing use of analgesic therapy by a cancer patient, the PD-1 inhibitor is administered at a dose of 5 mg to 1500 mg. In some embodiments, the PD-1 inhibitor is administered at a dose of 200 mg, 250 mg, 350 mg, 600 mg, 700 mg, or 1050 mg. In some embodiments, the PD-1 inhibitor is administered at a dose of 1 mg/kg to 20 mg/kg of the patient's body weight. In some embodiments, the PD-1 inhibitor is administered at a dose of 1 mg/kg, 3 mg/kg or 10 mg/kg of the patient's body weight. In some embodiments, the PD-1 inhibitor is administered as one or more doses, wherein each dose is administered two weeks, three weeks, four weeks, five weeks or six weeks after the immediately preceding dose. In some embodiments, the PD-1 inhibitor is administered intravenously, subcutaneously, or intraperitoneally.

Other embodiments of the present disclosure will become apparent from the detailed description below.

BRIEF DESCRIPTION OF THE DRAWINGS

FIG. 6A shows baseline score on QLQ-C30 functioning scales. FIG. 6B shows baseline score on QLQ-C30 symptom scales. FIG. 6C shows overall least squares (LS) mean change on QLQ-C30 functioning scales. FIG. 6D shows overall least squares (LS) mean change on QLQ-C30 symptom scales. *P<0.05 vs baseline; †Clinically meaningful change. CI, confidence interval; SD, standard deviation.

DETAILED DESCRIPTION

Figure 1:
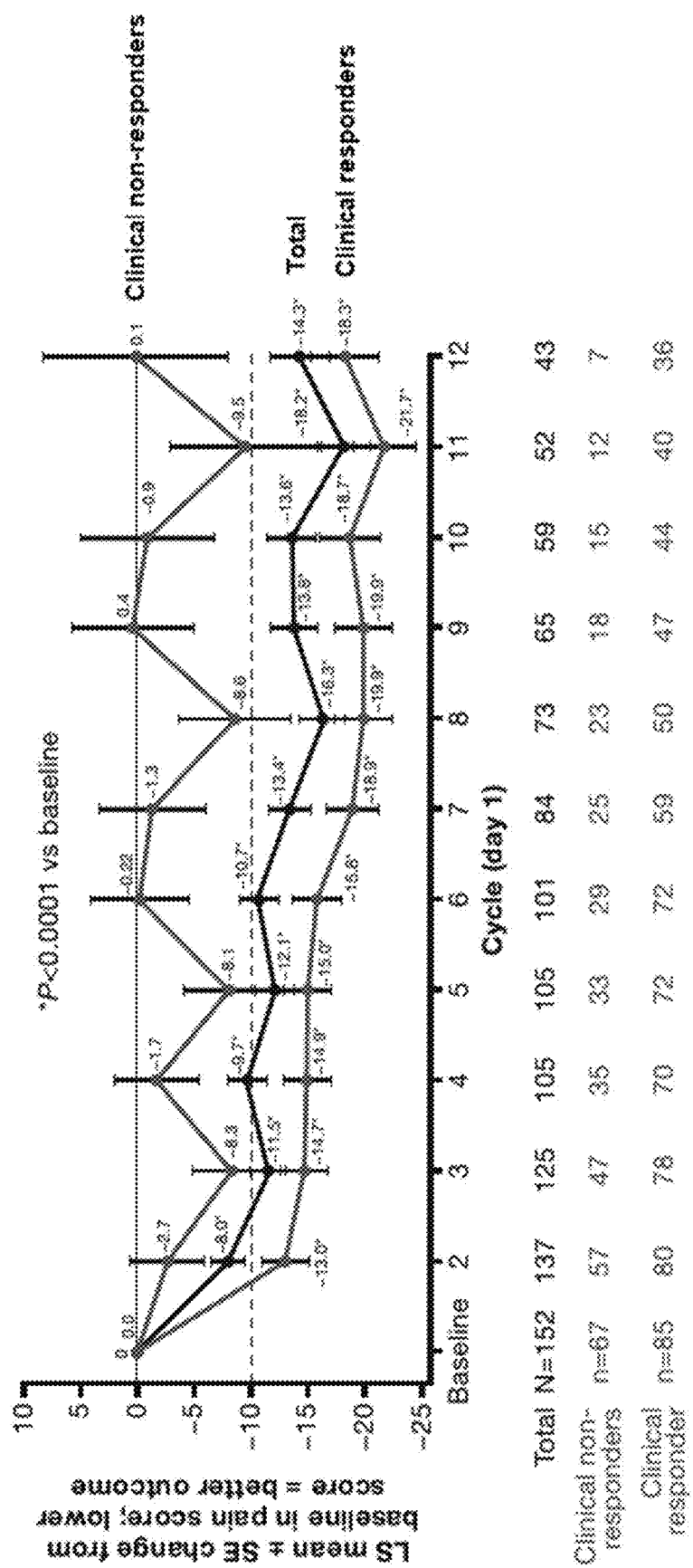
FIG. 1 shows the change from baseline in QLQ-C30 pain score by cycle among patients who had baseline and post-baseline assessment of the QLQ-C30 pain scale, in connection with the study described in Example 1 herein.

It is to be understood that the present disclosure is not limited to the particular methods and experimental conditions described, as such methods and conditions may vary. It is also to be understood that the terminology used herein is for the purpose of describing particular embodiments only, and is not intended to be limiting, and that the scope of the present disclosure will be limited only by the appended claims. Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, preferred methods and materials are now described. All publications mentioned herein are hereby incorporated by reference in their entirety unless otherwise stated.

The present disclosure generally relates to methods of treating or inhibiting cancer pain in a cancer patient, including selecting a patient suffering from cancer and pain, and administering to the patient a therapeutically effective amount of a programmed death 1 (PD-1) inhibitor. The present disclosure also relates to methods of treating or inhibiting the growth of a tumor and treating or inhibiting cancer pain, including selecting a patient suffering from cancer and pain, and administering to the patient a therapeutically effective amount of a PD-1 inhibitor. In some embodiments, the methods of the present disclosure lead to tumor regression and pain reduction concurrently—i.e., wherein such benefits are achieved in approximately the same amount of time. Throughout the present disclosure, references to particular anti-PD-1 antibodies are provided to illustrate a representative PD-1 inhibitor, and do not limit the scope of the disclosure.

Methods of Treating or Inhibiting Cancer Pain

The present disclosure includes methods of treating or inhibiting cancer pain, comprising selecting a patient with cancer and in need thereof; and administering to the patient an antibody or antigen-binding fragment thereof that specifically binds PD-1, PD-L1, and/or PD-L2, or any other "PD-1 inhibitor" as described herein.

As used herein, the terms "treating", "treat", or the like with respect to pain, mean to alleviate or reduce the severity of at least one symptom or indication, to eliminate the causation of symptoms either on a temporary or permanent basis, to inhibit pain, to reduce pain, and/or to reduce the need for opioids or other analgesics. The pain (sometimes referred to herein as "cancer pain") can originate from the patient's primary cancer itself or from other areas in the patient's body where the cancer has spread (metastases). Cancer pain may arise from injuries, infection or inflammation associated with the cancer. Cancer pain may arise from the physical effect of the cancer on a region of the patient's body or may be caused by chemicals secreted from cancerous cells and/or tissues due to the cancer itself and/or a cancer treatment. Cancer pain may include acute, chronic, and/or breakthrough pain. In related embodiments, the terms "treating", "treat", or the like with respect to tumor growth, mean to alleviate or reduce the severity of at least one symptom or indication, to eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, to eliminate the need for radiation or surgery, to increase duration of survival of the subject, and/or lead to stable disease (SD), partial response (PR) or complete response (CR) (as determined using RECIST criteria). In many embodiments, the terms "tumor", "lesion," "tumor lesion," "cancer," and "malignancy" are used interchangeably and refer to one or more cancerous growths.

As used herein, the expression "a subject in need thereof" with respect to treating or inhibiting cancer pain means a human or non-human mammal that has cancer and exhibits one or more symptoms or indications of pain, and who needs treatment for the same. The term "subject" may be interchangeably used with the term "patient". In some embodiments, the expression includes human subjects that have and/or need treatment for pain and also have and/or need treatment for a solid tumor, e.g., anal cancer, bladder cancer, bone cancer, breast cancer, brain cancer, cervical cancer, colon cancer, colorectal cancer, endometrial cancer, esophageal cancer, head and neck cancer, kidney cancer, liver cancer, lung cancer, myeloma, ovarian cancer, pancreatic cancer, prostate cancer, salivary gland cancer, skin cancer (CSCC and BCC), stomach cancer, testicular cancer, and uterine cancer.

In related embodiments, the expression includes subjects with primary or metastatic tumors (advanced malignancies). For example, a human subject may be diagnosed with a primary or a metastatic tumor and/or with one or more symptoms or indications including, but not limited to, pain, unexplained weight loss, general weakness, persistent fatigue, loss of appetite, fever, night sweats, bone or muscle pain, shortness of breath, swollen abdomen, chest pain/pressure, enlargement of spleen, and elevation in the level of a cancer-related biomarker.

The severity of a patient's pain may be assessed using standard methods known to those skilled in the art, such as the European Organization for Research and Treatment of Cancer (EORTC) cancer specific 30-item questionnaire (QLQ-C30) quality of life scale (Osoba et al., *J Clin Oncol.* 1998; 16:139-144), the Pain Intensity Numerical Rating Scale (NRS) score, the Roland Morris Disability Questionnaire (RMDQ) total score, or the Patient Global Assessment (PGA) of pain score (Mannion et al., *Nat. Clin. Pract. Rheumatol.*, 2007, 3:610-618). Other methods that may be used to measure pain intensity include: visual analogue scales (VASs), verbal rating scales (VRSs), and numerical rating scales (NRSs) (Von Korff et al., 2000, *Spine*, 25:3140-51; Zanoli et al., 2000, *Spine* 25:3178-85; Haefeli et al., 2006, *Eur Spine J*, 15 (Suppl 1): S17-S24; McGuire, 1999, INSTRUMENTS FOR HEALTH-CARE RESEARCH, 528-561 (Eds. Frank-Stromborg and Olsen); Ogon et al., 1996, *Pain*, 64:425-428; Hagg et al., 2003, *Eur Spine J*, 12:12-20; Jensen et al., 1986, *Pain*, 27:117-126).

The EORTC QLQ-C30 is one of the standard instruments used in oncology for the evaluation of new cancer therapies and provides a comprehensive assessment of the principal health-related QoL dimensions identified as relevant by cancer patients (physical functioning, emotional, cognitive, role, and social functioning, global QoL), and the impact of symptoms and toxicities. Scores range from 0 to 100; higher scores on functional domains and lower scores on symptoms reflect better outcomes. A change of at least 10 points absolute value from baseline is considered clinically meaningful (Osoba et al., *J Clin Oncol*, 1998; 16:139-144).

The SKINDEX-16 assesses the impact of skin disease on patients' health-related QoL over the past week with results reported on three subscales (symptom, emotional, and functional). SKINDEX-16 is a dermatology-specific measure that focuses on specific domains of disease burden as they relate to skin disease. Scores on the subscales range from 0 to 100; lower scores reflect lower impact of disease. A change 10 points is considered clinically meaningful (Hansson et al., *Eur J Dermatol.*, 2018; 28:775-783).

In some embodiments, the disclosed methods of treating or inhibiting cancer pain lead to one or more of the following effects: reduction of pain, improvement in quality of life, reduction in the use of analgesics such as opioids (including concomitant or background analgesic therapy), and reduction of tumor cells.

In certain embodiments, the methods of the present disclosure are used in a subject with a solid tumor. As used herein, the term "solid tumor" refers to an abnormal mass of tissue that usually does not contain cysts or liquid areas. Solid tumors may be benign (not cancer) or malignant (cancer). For the purposes of the present disclosure, the term "solid tumor" means malignant solid tumor. The term includes different types of solid tumors named for the cell types that form them, viz. sarcomas, carcinomas and lymphomas. However, the term does not include leukemias. In various embodiments, the term "solid tumor" includes cancers arising from connective or supporting tissue (e.g., bone or muscle) (referred to as sarcomas), cancers arising from the body's glandular cells and epithelial cells which line body tissues (referred to as carcinomas), and cancers of the lymphoid organs such as lymph nodes, spleen and thymus (referred to as lymphomas). Lymphoid cells occur in almost all tissues of the body and therefore, lymphomas may develop in a wide variety of organs. In certain embodiments, the term "solid tumor" includes cancers including, but not limited to, BCC, CSCC, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma. In certain embodiments, the term "solid tumor" includes cancers including, but not limited to, hepatocellular carcinoma, non-small cell lung cancer, head and neck squamous cell cancer, basal cell carcinoma, breast carcinoma, cutaneous squamous cell carcinoma, chondrosarcoma, angiosarcoma, cholangiocarcinoma, soft tissue sarcoma, colorectal cancer, melanoma, Merkel cell carcinoma, and glioblastoma multiforme. In certain embodiments, the term "solid tumor" comprises more than one solid tumor lesions located separate from one another, e.g., 2, more than 2, more than 5, more than 10, more than 15, more than 20, or more than 25 lesions in a subject in need of treatment. In certain embodiments, the more than one lesions are located distally from one another in the same organ. In certain other embodiments, the tumor lesions may be located in different organs.

According to certain embodiments, the present disclosure includes methods for treating or inhibiting pain in a cancer patient. In some embodiments, the disclosed methods reduce opioid use by the patient. In some embodiments, the disclosed methods treat or inhibit tumor growth concurrently with reducing pain in the patient.

In certain embodiments, the methods comprise administering a therapeutically effective amount of a PD-1 inhibitor in combination with an analgesic therapy. Analgesic therapies include, but are not limited to, opioids (e.g., fentanyl, oxycodone, hydrocodone, hydromorphone, codeine, morphine, meperidine, methadone), non-steroidal anti-inflammatory drugs (NSAIDs), acetaminophen, steroids, and combinations thereof. In one embodiment, the analgesic therapy comprises an opioid.

In certain embodiments, the methods comprise administering a therapeutically effective amount of a PD-1 inhibitor in combination with an analgesic therapy and an anti-tumor therapy. Anti-tumor therapies include, but are not limited to, conventional anti-tumor therapies such as chemotherapy, radiation, surgery, and other anti-tumor therapies.

The methods of the present disclosure, according to certain embodiments, include administering to a subject a therapeutically effective amount of a PD-1 inhibitor (e.g., an anti-PD-1 antibody or antigen-binding fragment thereof) in combination with an additional therapeutic agent or therapy. The additional therapeutic agent or therapy may be administered for reducing pain, for increasing anti-tumor efficacy, for reducing toxic effects of one or more therapies and/or for reducing the dosage of one or more therapies. In various embodiments, the additional therapeutic agent or therapy may include one or more of: radiation, surgery, a cancer vaccine, imiquimod, an anti-viral agent (e.g., cidofovir), photodynamic therapy, HHI therapy (e.g., vismodegib, sonedegib), a programmed death ligand 1 (PD-L1) inhibitor (e.g., an anti-PD-L1 antibody), a lymphocyte activation gene 3 (LAG3) inhibitor (e.g., an anti-LAG3 antibody), a cytotoxic T-lymphocyte-associated protein 4 (CTLA-4) inhibitor (e.g., ipilimumab), a glucocorticoid-induced tumor necrosis factor receptor (GITR) agonist (e.g., an anti-GITR antibody), a T-cell immunoglobulin and mucin containing-3 (TIM3) inhibitor, a B- and T-lymphocyte attenuator (BTLA) inhibitor, a T-cell immunoreceptor with Ig and ITIM domains (TIGIT) inhibitor, a CD38 inhibitor, a CD47 inhibitor, an indoleamine-2,3-dioxygenase (IDO) inhibitor, a CD28 activator, a vascular endothelial growth factor (VEGF) antagonist [e.g., a "VEGF-Trap" such as aflibercept, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an angiopoietin-2 (Ang2) inhibitor, a transforming growth factor beta (TGFβ) inhibitor, an epidermal growth factor receptor (EGFR) inhibitor, an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin), granulocyte-macrophage colony-stimulating factor (GM-CSF), an oncolytic virus, a cytotoxin, a chemotherapeutic agent (e.g., pemetrexed, dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, topotecan, irinotecan, vinorelbine, and vincristine), vismodegib, sonedegib, an IL-6R inhibitor, an IL-4R inhibitor, an IL-10 inhibitor, a cytokine such as IL-2, IL-7, IL-12, IL-21, and IL-15, an antibody drug conjugate, an oncolytic virus, an anti-inflammatory drug such as a corticosteroid, an analgesic, a non-steroidal anti-inflammatory drug (NSAID), an opioid, and a dietary supplement such as an antioxidant, and combinations thereof.

As used herein, the expression "in combination with" refers to the co-administration of a PD-1 inhibitor disclosed herein (e.g., an anti-PD-1 antibody) and a second therapeutic agent or therapy to a subject. In some embodiments, the co-administration is concurrent. In other embodiments, the PD-1 inhibitor is administered prior to the additional therapeutic agent or therapy. In other embodiments, the PD-1 inhibitor is administered after the additional therapeutic agent or therapy.

In certain embodiments, the present disclosure includes methods to treat or inhibit pain, the methods comprising: (a) selecting a cancer patient suffering from pain, wherein the patient is selected based on one or more of the following attributes: (i) the patient has CSCC; (ii) the patient has one or more tumor lesions; (iii) the tumor is unresectable; (iv) the patient is not a suitable candidate for surgery and/or radiation therapy; (v) the patient has metastatic or locally advanced CSCC; (vi) the patient has an Eastern Cooperative Oncology Group (ECOG) performance status of less than or equal to 1; (vii) the patient is on a standard of care pain medication (such as an opioid); (viii) the patient exhibits a high score for pain on a Quality of Life (QoL) questionnaire; and (ix) the tumor comprises UV-induced DNA damage; and (b) administering a therapeutically effective amount of a PD-1 inhibitor (e.g., an anti-PD-1 antibody or antigen-binding fragment thereof) to the patient in need thereof.

In certain embodiments, the methods of the present disclosure comprise administering to a subject in need thereof a therapeutically effective amount of a PD-1 inhibitor (e.g., an anti-PD-1 antibody or antigen-binding fragment thereof), wherein administration of the PD-1 inhibitor leads to reduced cancer pain. In certain embodiments, pain is reduced by at least about 10%, about 20%, about 30%, about 40%, about 50%, about 60%, about 70%, about 80% or more as compared to the baseline level of pain experienced by the patient prior to administration of the PD-1 inhibitor. In certain embodiments, pain is reduced by at least 50% within 2 months, 4 months, 6 months, 8 months, 10 months, or 1 year after administration of the PD-1 inhibitor. In certain embodiments, pain is reduced by at least 60% within 2 months, 4 months, 6 months, 8 months, 10 months, or 1 year after administration of the PD-1 inhibitor. In certain embodiments, pain is reduced by at least 70% within 2 months, 4 months, 6 months, 8 months, 10 months, or 1 year after administration of the PD-1 inhibitor. In certain embodiments, pain is reduced by at least 80% within 2 months, 4 months, 6 months, 8 months, 10 months, or 1 year after administration of the PD-1 inhibitor. In certain embodiments, pain is reduced by at least 90% within 2 months, 4 months, 6 months, 8 months, 10 months, or 1 year after administration of the PD-1 inhibitor. As used herein, "administration of the PD-1 inhibitor" may refer to the initiation of an administration regimen (e.g., one or more doses or cycles, as described herein) of the PD-1 inhibitor.

In certain embodiments, the methods of the present disclosure comprise administering to a subject in need thereof a therapeutically effective amount of a PD-1 inhibitor (e.g., an anti-PD-1 antibody or antigen-binding fragment thereof), wherein administration of the PD-1 inhibitor leads to one or more of the following: (i) treats, or inhibits the growth of a tumor; (ii) promotes tumor regression; (iii) reduces tumor cell load or tumor burden; (iv) prevents tumor recurrence; (v) partial response (PR) or complete response (CR) as determined using RECIST criteria; (vi) increased overall survival or progression-free survival; (vii) reduces pain in the patient by about 20%, 30%, 40%, 50% or more as compared to the baseline; (viii) leads to reduced use of analgesic therapy by the patient; and/or (ix) increases quality of life, as determined by QoL questionnaire analysis.

In certain embodiments, the methods of the present disclosure comprise administering to a subject in need thereof a therapeutically effective amount of a PD-1 inhibitor (e.g., an anti-PD-1 antibody or antigen-binding fragment thereof), wherein administration of the PD-1 inhibitor concurrently leads to reduced cancer pain (e.g., reduced by at least about 10%, about 20%, about 30%, about 40%, about 50%, about 60%, about 70%, or about 80%) and complete disappearance of all evidence of tumor cells ("complete response"). In certain embodiments, administration of the anti-PD-1 antibody concurrently leads to reduced cancer pain (e.g., reduced by at least about 10%, about 20%, about 30%, about 40%, about 50%, about 60%, about 70%, or about 80%) and at least 30% decrease in tumor cells or tumor size ("partial response"). Tumor reduction can be measured by any methods known in the art, e.g., X-rays, positron emission tomography (PET), computed tomography (CT), magnetic resonance imaging (MRI), cytology, histology, or molecular genetic analyses. As used herein, the term "concurrently" refers to the benefits of treatment or inhibition of pain coinciding with the benefits of treatment or inhibition of tumor growth, wherein both types of benefits are achieved at approximately the same time—e.g., within 1 week, 2 weeks, 3 weeks, 1 month, 2 months, 3 months, 4 months, 5 months, or 6 months of each other.

In certain embodiments, the methods of the present disclosure comprise selecting a cancer patient with pain, and administering to the patient a therapeutically effective amount of a PD-1 inhibitor (e.g., an anti-PD-1 antibody or antigen-binding fragment thereof), wherein administration of the PD-1 inhibitor leads to increased overall survival (OS) or progression-free survival (PFS) of the patient as compared to a patient administered with a 'standard-of-care' (SOC) analgesic therapy (e.g., opioid or NSAID). In certain embodiments, the PFS is increased by at least one month, at least 2 months, at least 3 months, at least 4 months, at least 5 months, at least 6 months, at least 7 months, at least 8 months, at least 9 months, at least 10 months, at least 11 months, at least 1 year, at least 2 years, or at least 3 years as compared to a patient administered with any one or more SOC therapies. In certain embodiments, the OS is increased by at least one month, at least 2 months, at least 3 months, at least 4 months, at least 5 months, at least 6 months, at least 7 months, at least 8 months, at least 9 months, at least 10 months, at least 11 months, at least 1 year, at least 2 years, or at least 3 years as compared to a patient administered with any one or more SOC therapies.

In certain embodiments, the methods of the present disclosure comprise administering to a subject in need thereof a therapeutically effective amount of a PD-1 inhibitor (e.g., an anti-PD-1 antibody or antigen-binding fragment thereof), wherein the subject is a cancer patient and the administration of the PD-1 inhibitor leads to reduced opioid use by the cancer patient. In certain embodiments, opioid use is reduced by at least about 10%, about 20%, about 30%, about 40%, or about 50% as compared to an untreated subject or a subject administered another anti-tumor therapy. In certain embodiments, opioid use is reduced by at least 20% within 4 months, 6 months, 8 months, 10 months, or 1 year after administration of a first dose of the PD-1 inhibitor. In certain embodiments, opioid use is reduced by at least 30% within 4 months, 6 months, 8 months, 10 months, or 1 year after administration of a first dose of the PD-1 inhibitor. In certain embodiments, opioid use is reduced by at least 40% within 4 months, 6 months, 8 months, 10 months, or 1 year after administration of a first dose of the PD-1 inhibitor. In certain embodiments, opioid use is reduced by at least 50% within 4 months, 6 months, 8 months, 10 months, or 1 year after administration of a first dose of the PD-1 inhibitor.

The present disclosure also provides kits comprising a PD-1 inhibitor (e.g., an anti-PD-1 antibody or antigen-binding fragment thereof) for therapeutic uses as described herein. Kits typically include a label indicating the intended use of the contents of the kit and instructions for use. As used herein, the term "label" includes any writing, or recorded material supplied on, in or with the kit, or which otherwise accompanies the kit. Accordingly, this disclosure provides a kit for treating a subject afflicted with a cancer and suffering from pain, the kit comprising: (a) a therapeutically effective dosage of a PD-1 inhibitor antibody; and (b) instructions for using the PD-1 inhibitor in any of the methods disclosed herein. In certain embodiments for treating human patients, the kit comprises a PD-1 inhibitor disclosed herein, e.g., cemiplimab, nivolumab, or pembrolizumab. In some embodiments, the instructions include instructions for administering the PD-1 inhibitor to treat or inhibit pain.

Methods of Reducing Analgesic Use

The present disclosure includes methods of reducing analgesic (e.g., opioid) use, comprising selecting a cancer patient suffering from pain wherein the patient is being treated with analgesic therapy (i.e., as a background medication) to manage the patient's pain; and administering to the patient an antibody or antigen-binding fragment thereof that specifically binds PD-1, PD-L1, and/or PD-L2, or any other "PD-1 inhibitor" as described herein. In some embodiments, the method reduces the patient's use of the analgesic, or reduces the need for analgesic therapy, by reducing the patient's pain. In general, the reduction of analgesic use is measured as a comparison from the initial baseline use before administration of the PD-1 inhibitor, and at a time point after administration of the PD-1 inhibitor (e.g., after initiation of an administration regimen (e.g., one or more doses or cycles, as described herein). In some embodiments, the amount of analgesic therapy received by the cancer patient being treated with a PD-1 inhibitor is less than the amount of analgesic therapy received by a cancer patient not treated with a PD-1 inhibitor.

In some embodiments, the disclosed methods of reducing analgesic use comprise selecting a patient with cancer wherein the patient is receiving analgesic therapy as a concomitant or background medication to manage pain; and administering a therapeutically effective amount of a PD-1 inhibitor to the patient. In general, the analgesic therapy is administered to manage the patient's pain, e.g., prior to administration of the PD-1 inhibitor. In some embodiments, the analgesic therapy is an opioid. In some embodiments, the disclosed methods reduce the amount of analgesic therapy received by the patient by 20%, 30%, 40%, 50% or more as compared to the baseline amount of analgesic therapy received by the patient prior to administration of the PD-1 inhibitor. As used herein, "administration of the PD-1 inhibitor" may refer to the initiation of an administration regimen (e.g., one or more doses or cycles, as described herein) of the PD-1 inhibitor. In some embodiments, the amount of analgesic therapy is reduced by 20%, 30%, 40%, 50% or more within 4 months, 6 months, 8 months, 10 months, or 1 year after administration of the PD-1 inhibitor while maintaining a continuing regimen of administration of the PD-1 inhibitor. In some embodiments, the disclosed methods of reducing analgesic use lead to reduced cancer pain as the patient is receiving less analgesic therapy while maintaining a continuing regimen of administration of the PD-1 inhibitor. In one embodiment, the use of analgesic therapy is eliminated or withdrawn upon administration of one or more doses of the PD-1 inhibitor.

In some embodiments, the disclosed methods include reducing the use of an analgesic selected from one or more of an opioid, NSAID, acetaminophen, a steroid, and combinations thereof. In some embodiments, the analgesic comprises an opioid. In some embodiments, the opioid is selected from fentanyl, oxycodone, hydrocodone, hydromorphone, codeine, morphine, meperidine, and methadone.

In certain embodiments, the methods of the present disclosure comprise administering to a subject in need thereof a therapeutically effective amount of a PD-1 inhibitor (e.g., an anti-PD-1 antibody or antigen-binding fragment thereof), wherein the subject is a cancer patient and the administration of the PD-1 inhibitor leads to reduced opioid use by the cancer patient. In certain embodiments, opioid use is reduced by at least about 10%, about 20%, about 30%, about 40%, or about 50% as compared to an untreated subject or a subject administered another anti-tumor therapy. In certain embodiments, opioid use is reduced by at least 20% within 4 months, 6 months, 8 months, 10 months, or 1 year after administration of a first dose of the PD-1 inhibitor. In certain embodiments, opioid use is reduced by at least 30% within 4 months, 6 months, 8 months, 10 months, or 1 year after administration of a first dose of the PD-1 inhibitor. In certain embodiments, opioid use is reduced by at least 40% within 4 months, 6 months, 8 months, 10 months, or 1 year after administration of a first dose of the PD-1 inhibitor. In certain embodiments, opioid use is reduced by at least 50% within 4 months, 6 months, 8 months, 10 months, or 1 year after administration of a first dose of the PD-1 inhibitor.

In certain embodiments, the methods of the present disclosure comprise administering to a subject in need thereof a therapeutically effective amount of a PD-1 inhibitor (e.g., an anti-PD-1 antibody or antigen-binding fragment thereof), wherein administration of the PD-1 inhibitor concurrently leads to reduced cancer pain (e.g., reduced by at least about 10%, about 20%, about 30%, about 40%, about 50%, about 60%, about 70%, or about 80%) and complete disappearance of all evidence of tumor cells ("complete response"). In certain embodiments, administration of the anti-PD-1 antibody concurrently leads to reduced cancer pain (e.g., reduced by at least about 10%, about 20%, about 30%, about 40%, about 50%, about 60%, about 70%, or about 80%) and at least 30% decrease in tumor cells or tumor size ("partial response"). Tumor reduction can be measured by any methods known in the art, e.g., X-rays, positron emission tomography (PET), computed tomography (CT), magnetic resonance imaging (MRI), cytology, histology, or molecular genetic analyses. As used herein, the term "concurrently" refers to the benefits of treatment or inhibition of pain coinciding with the benefits of treatment or inhibition of tumor growth, wherein both types of benefits are achieved at approximately the same time—e.g., within 1 week, 2 weeks, 3 weeks, 1 month, 2 months, 3 months, 4 months, 5 months, or 6 months of each other.

The present disclosure also provides kits comprising a PD-1 inhibitor (e.g., an anti-PD-1 antibody or antigen-binding fragment thereof) for therapeutic uses as described herein. Kits typically include a label indicating the intended use of the contents of the kit and instructions for use. As used herein, the term "label" includes any writing, or recorded material supplied on, in or with the kit, or which otherwise accompanies the kit. Accordingly, this disclosure provides a kit for treating a subject afflicted with a cancer and pain, the kit comprising: (a) a therapeutically effective dosage of a PD-1 inhibitor antibody; and (b) instructions for using the PD-1 inhibitor in any of the methods disclosed herein. In certain embodiments for treating human patients, the kit comprises a PD-1 inhibitor disclosed herein, e.g., cemiplimab, nivolumab, or pembrolizumab. In some embodiments, the instructions include instructions for administering the PD-1 inhibitor to treat or inhibit pain and to treat or inhibit the growth of a tumor.

PD-1 Inhibitors

The methods disclosed herein include administering a therapeutically effective amount of a PD-1 inhibitor. As used herein, a "PD-1 inhibitor" refers to any molecule capable of inhibiting, blocking, abrogating or interfering with the activity or expression of PD-1. In some embodiments, the PD-1 inhibitor can be an antibody, a small molecule compound, a nucleic acid, a polypeptide, or a functional fragment or variant thereof. Non-limiting examples of suitable PD-1 inhibitor antibodies include anti-PD-1 antibodies and antigen-binding fragments thereof, anti-PD-L1 antibodies and antigen-binding fragments thereof, and anti-PD-L2 antibodies and antigen-binding fragments thereof. Other non-limiting examples of suitable PD-1 inhibitors include RNAi molecules such as anti-PD-1 RNAi molecules, anti-PD-L1 RNAi, and an anti-PD-L2 RNAi, antisense molecules such as anti-PD-1 antisense RNA, anti-PD-L1 antisense RNA, and anti-PD-L2 antisense RNA, and dominant negative proteins such as a dominant negative PD-1 protein, a dominant negative PD-L1 protein, and a dominant negative PD-L2 protein. Some examples of the foregoing PD-1 inhibitors are described in e.g., U.S. Pat. No. 9,308,236, U.S. Ser. No. 10/011,656, and US 20170290808, the portions of which that identify PD-1 inhibitors are hereby incorporated by reference.

The term "antibody," as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains CH1, CH2 and CH3). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences or may be naturally or artificially modified. An amino acid consensus sequence may be defined based on a side-by-side analysis of two or more CDRs. The term "antibody," as used herein, also includes antigen-binding fragments of full antibody molecules.

As used herein, the terms "antigen-binding fragment" of an antibody, "antigen-binding portion" of an antibody, and the like, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The antibodies used in the methods disclosed herein may be human antibodies. As used herein, the term "human antibody" refers to antibodies having variable and constant regions derived from human germline immunoglobulin sequences. The human antibodies of the present disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods disclosed herein may be recombinant human antibodies. As used herein, the term "recombinant human antibody" includes all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., 1992, *Nucl. Acids Res.,* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Anti-PD-1 Antibodies and Antigen-Binding Fragments Thereof

In some embodiments, PD-1 inhibitors used in the methods disclosed herein are antibodies or antigen-binding fragments thereof that specifically bind PD-1. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PD-1, as used in the context of the present disclosure, includes antibodies that bind PD-1 or a portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PD-1 may, however, have cross-reactivity to other antigens, such as PD-1 molecules from other (non-human) species.

According to certain exemplary embodiments, the anti-PD-1 antibody, or antigen-binding fragment thereof comprises a heavy chain variable region (HCVR), light chain variable region (LCVR), and/or complementarity determining regions (CDRs) comprising the amino acid sequences of any of the anti-PD-1 antibodies set forth in U.S. Pat. No. 9,987,500, which is hereby incorporated by reference in its entirety. In certain exemplary embodiments, the anti-PD-1 antibody or antigen-binding fragment thereof that can be used in the context of the present disclosure comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-PD-1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-PD-1 antibody or antigen-binding fragment thereof comprises an HCVR comprising SEQ ID NO: 1 and an LCVR comprising SEQ ID NO: 2. In certain embodiments, the methods of the present disclosure comprise the use of an anti-PD-1 antibody, wherein the antibody comprises a heavy chain comprising the amino acid sequence of SEQ ID NO: 9. In some embodiments, the anti-PD-1 antibody comprises a light chain comprising the amino acid sequence of SEQ ID NO: 10. An exemplary antibody comprising a heavy chain variable region comprising the amino acid sequence of SEQ ID NO: 1 and a light chain variable region comprising the amino acid sequence of SEQ ID NO: 2 is the fully human anti-PD-1 antibody known as cemiplimab (also known as REGN2810; LIBTAYO®).

According to certain exemplary embodiments, the methods of the present disclosure comprise the use of cemiplimab or a bioequivalent thereof. As used herein, the term "bioequivalent" refers to anti-PD-1 antibodies or PD-1-binding proteins or fragments thereof that are pharmaceutical equivalents or pharmaceutical alternatives whose rate and/or extent of absorption do not show a significant difference with that of a reference antibody (e.g., cemiplimab) when administered at the same molar dose under similar experimental conditions, either single dose or multiple dose. In the context of the present disclosure, the term "bioequivalent" includes antigen-binding proteins that bind to PD-1 and do not have clinically meaningful differences with cemiplimab with respect to safety, purity and/or potency.

According to certain embodiments of the present disclosure, the anti-human PD-1, or antigen-binding fragment thereof, comprises a HCVR having 90%, 95%, 98% or 99% sequence identity to SEQ ID NO: 1.

According to certain embodiments of the present disclosure, the anti-human PD-1, or antigen-binding fragment thereof, comprises a LCVR having 90%, 95%, 98% or 99% sequence identity to SEQ ID NO: 2.

According to certain embodiments of the present disclosure, the anti-human PD-1, or antigen-binding fragment thereof, comprises a HCVR comprising an amino acid sequence of SEQ ID NO: 1 having no more than 5 amino acid substitutions. According to certain embodiments of the present disclosure, the anti-human PD-1, or antigen-binding fragment thereof, comprises a LCVR comprising an amino acid sequence of SEQ ID NO: 2 having no more than 2 amino acid substitutions.

Sequence identity may be measured by methods known in the art (e.g., GAP, BESTFIT, and BLAST).

The present disclosure also includes use of anti-PD-1 antibodies or antigen-binding fragments thereof in methods to treat cancer, wherein the anti-PD-1 antibodies or antigen-binding fragments thereof comprise variants of any of the HCVR, LCVR and/or CDR amino acid sequences disclosed herein having one or more conservative amino acid substitutions. For example, the present disclosure includes use of anti-PD-1 antibodies or antigen-binding fragments thereof having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

Other anti-PD-1 antibodies or antigen-binding fragments thereof that can be used in the context of the methods of the present disclosure include, e.g., the antibodies referred to and known in the art as nivolumab, pembrolizumab, MEDI0608, pidilizumab, BI 754091, spartalizumab (also known as PDR001), camrelizumab (also known as SHR-1210), JNJ-63723283, MCLA-134, or any of the anti-PD-1 antibodies set forth in U.S. Pat. Nos. 6,808,710, 7,488,802, 8,008,449, 8,168,757, 8,354,509, 8,609,089, 8,686,119, 8,779,105, 8,900,587, and 9,987,500, and in WO 2006121168 and WO 2009114335. The portions of all of the aforementioned publications that identify anti-PD-1 antibodies are hereby incorporated by reference.

The anti-PD-1 antibodies used in the context of the methods of the present disclosure may have pH-dependent binding characteristics. For example, an anti-PD-1 antibody for use in the methods of the present disclosure may exhibit reduced binding to PD-1 at acidic pH as compared to neutral pH. Alternatively, an anti-PD-1 antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to PD-1 at acidic pH as compared to neutral pH" is expressed in terms of a ratio of the $K_D$ value of the antibody binding to PD-1 at acidic pH to the $K_D$ value of the antibody binding to PD-1 at neutral pH (or vice versa). For example, an antibody or antigen-binding fragment thereof may be regarded as exhibiting "reduced binding to PD-1 at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Anti-PD-L1 Antibodies and Antigen-Binding Fragments Thereof

In some embodiments, PD-1 inhibitors used in the methods disclosed herein are antibodies or antigen-binding fragments thereof that specifically bind PD-L1. For example, an antibody that "specifically binds" PD-L1, as used in the context of the present disclosure, includes antibodies that bind PD-L1 or a portion thereof with a $K_D$ of about $1 \times 10^{-8}$ M or less (e.g., a smaller $K_D$ denotes a tighter binding). A "high affinity" anti-PD-L1 antibody refers to those mAbs having a binding affinity to PD-L1, expressed as $K_D$ of at least $10^{-8}$ M, preferably $10^{-9}$ M, more preferably $10^{-10}$ M, even more preferably $10^{-11}$ M, even more preferably $10^{-12}$ M, as measured by surface plasmon resonance, e.g., BIACORE™ or solution-affinity ELISA. An isolated antibody that specifically binds human PD-L1 may, however, have cross-reactivity to other antigens, such as PD-L1 molecules from other (non-human) species.

According to certain exemplary embodiments, the anti-PD-L1 antibody or antigen-binding fragment thereof comprises a heavy chain variable region (HCVR), light chain variable region (LCVR), and/or complementarity determining regions (CDRs) comprising the amino acid sequences of any of the anti-PD-L1 antibodies set forth in U.S. Pat. No. 9,938,345, which is hereby incorporated by reference in its entirety. In certain exemplary embodiments, an anti-PD-L1 antibody or antigen-binding fragment thereof that can be used in the context of the present disclosure comprises the heavy chain complementarity determining regions (HCDRs) of a heavy chain variable region (HCVR) comprising SEQ ID NO: 11 and the light chain complementarity determining regions (LCDRs) of a light chain variable region (LCVR) comprising SEQ ID NO: 12. An exemplary anti-PD-L1 antibody comprising a HCVR of SEQ ID NO: 11 and a LCVR of SEQ ID NO: 12 is REGN3504.

According to certain embodiments of the present disclosure, the anti-human PD-L1 antibody, or antigen-binding fragment thereof, comprises a HCVR having 90%, 95%, 98% or 99% sequence identity to SEQ ID NO: 11. According to certain embodiments of the present disclosure, the anti-human PD-L1 antibody, or antigen-binding fragment thereof, comprises a LCVR having 90%, 95%, 98% or 99% sequence identity to SEQ ID NO: 12.

According to certain embodiments of the present disclosure, the anti-human PD-L1 antibody, or antigen-binding fragment thereof, comprises a HCVR comprising an amino acid sequence of SEQ ID NO: 11 having no more than 5 amino acid substitutions. According to certain embodiments of the present disclosure, the anti-human PD-L1 antibody, or antigen-binding fragment thereof, comprises a LCVR comprising an amino acid sequence of SEQ ID NO: 12 having no more than 2 amino acid substitutions.

Sequence identity may be measured by methods known in the art (e.g., GAP, BESTFIT, and BLAST).

The present disclosure also includes use of anti-PD-L1 antibodies in methods to treat cancer, wherein the anti-PD-L1 antibodies comprise variants of any of the HCVR, LCVR and/or CDR amino acid sequences disclosed herein having one or more conservative amino acid substitutions. For example, the present disclosure includes use of anti-PD-L1 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

Other anti-PD-L1 antibodies that can be used in the context of the methods of the present disclosure include, e.g., the antibodies referred to and known in the art as MDX-1105, atezolizumab (TECENTRIQ™), durvalumab (IMFINZI™), avelumab (BAVENCIO™), LY3300054, FAZ053, STI-1014, CX-072, KN035 (Zhang et al., Cell Discovery, 3, 170004 (March 2017)), CK-301 (Gorelik et al., American Association for Cancer Research Annual Meeting (AACR), 2016 Apr. 4 Abstract 4606), or any of the other anti-PD-L1 antibodies set forth in patent publications U.S. Pat. Nos. 7,943,743, 8,217,149, 9,402,899, 9,624,298, 9,938,345, WO 2007005874, WO 2010077634, WO 2013181452, WO 2013181634, WO 2016149201, WO 2017034916, or EP3177649. The portions of all of the aforementioned publications that identify anti-PD-L1 antibodies are hereby incorporated by reference.

Pharmaceutical Compositions and Administration

The present disclosure provides therapeutic pharmaceutical compositions comprising the PD-1 inhibitors disclosed herein. Such pharmaceutical compositions may be formulated with suitable pharmaceutically acceptable carriers, excipients, buffers, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al., "Compendium of excipients for parenteral formulations" PDA, *J Pharm Sci Technol* 52:238-311 (1998).

The dose of PD-1 inhibitor (e.g., anti-PD-1 antibody or antigen-binding fragment thereof) may vary depending upon the age and the size of a subject to be administered, target disease, conditions, route of administration, and the like. When a PD-1 inhibitor of the present disclosure is used for treating or inhibiting cancer pain and/or treating or inhibiting the growth of a tumor, it may be advantageous to administer the PD-1 inhibitor at a single dose of about 0.1 to about 100 mg/kg body weight. Depending on the severity of the condition, the frequency and the duration of the treatment can be adjusted. In certain embodiments, the PD-1 inhibitor of the present disclosure can be administered as an initial dose of at least about 0.1 mg to about 1500 mg, about 1 to about 1200 mg, about 5 to about 1000 mg, or about 10 to about 800 mg. In certain embodiments, the initial dose may be followed by administration of a second or a plurality of subsequent doses of the PD-1 inhibitor in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., (1987) *J. Biol. Chem.* 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. The pharmaceutical composition can be also delivered in a vesicle, in particular a liposome (see, e.g., Langer (1990) *Science* 249:1527-1533).

The use of nanoparticles to deliver the PD-1 inhibitor of the present disclosure is also contemplated herein. Antibody-conjugated nanoparticles may be used both for therapeutic and diagnostic applications. Antibody-conjugated nanoparticles and methods of preparation and use are described in detail by Arruebo et al., 2009, "Antibody-conjugated nanoparticles for biomedical applications," *J. Nanomat.*, Vol. 2009, Article ID 439389, 24 pages. Nanoparticles may be developed and conjugated to antibodies contained in pharmaceutical compositions to target cells. Nanoparticles for drug delivery have also been described in, for example, U.S. Pat. Nos. 8,257,740, or 8,246,995.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracranial, intraperitoneal and intramuscular injections, drip infusions, etc. These injectable preparations may be prepared by methods publicly known.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

In certain embodiments, the present disclosure provides a pharmaceutical composition or formulation comprising a therapeutic amount of a PD-1 inhibitor (e.g., an anti-PD-1 antibody or antigen-binding fragment thereof) and a pharmaceutically acceptable carrier. Non-limiting examples of pharmaceutical compositions comprising an anti-PD-1 antibody that can be used in the context of the present disclosure are disclosed in US 20190040137.

Administration Regimens

In certain embodiments, the methods disclosed herein include administering to a subject in need thereof a therapeutically effective amount of a PD-1 inhibitor (e.g., an anti-PD-1 antibody or antigen-binding fragment thereof) in multiple doses, e.g., as part of a specific therapeutic dosing regimen. For example, the therapeutic dosing regimen may comprise administering one or more doses of a PD-1 inhibitor to the subject at a frequency of about once a day, once every two days, once every three days, once every four days, once every five days, once every six days, once a week, once every two weeks, once every three weeks, once every four weeks, once every five weeks, once every six weeks, once every eight weeks, once every twelve weeks, once a month, once every two months, once every three months, once every four months, twice a day, twice every two days, twice every three days, twice every four days, twice every five days, twice every six days, twice a week, twice every two weeks, twice every three weeks, twice every four weeks, twice every five weeks, twice every six weeks, twice every eight weeks, twice every twelve weeks, twice a month, twice every two months, twice every three months, twice every four months, three times a day, three times every two days, three times every three days, three times every four days, three times every five days, three times every six days, three times a week, three times every two weeks, three times every three weeks, three times every four weeks, three times every five weeks, three times every six weeks, three times every eight weeks, three times every twelve weeks, three times a month, three times every two months, three times every three months, three times every four months or less frequently or as needed so long as a therapeutic response is achieved. In one embodiment, one or more doses of a PD-1 inhibitor are administered once every three weeks.

In certain embodiments, the one or more doses are administered in at least one treatment cycle. The methods, according to this aspect, comprise administering to a subject in need thereof at least one treatment cycle comprising administration of 1, 2, 3, 4, 5, 6, 7, 8, 9, 10 or more doses of a PD-1 inhibitor (e.g., an anti-PD-1 antibody or antigen-binding fragment thereof). In one embodiment, a treatment cycle comprises 12 doses of a PD-1 inhibitor. In one embodiment, a treatment cycle comprises 24 doses of a PD-1 inhibitor. In some embodiments, 1, 2, 3, 4, 5, 6, 7, 8, 9, 10 or more treatment cycles may be administered to a subject in need thereof.

In certain embodiments, one or more doses of the PD-1 inhibitor are administered 1 to 12 weeks after the immediately preceding dose, for example, 1, 2, 3, 4, 5, 6, 7, 8, 9, 10, 11 or 12 weeks after the immediately preceding dose.

Dosage

The amount of PD-1 inhibitor (e.g., an anti-PD-1 antibody or antigen-binding fragment thereof) administered to a subject according to the methods disclosed herein is, generally, a therapeutically effective amount. As used herein, the term "therapeutically effective amount" means an amount of a PD-1 inhibitor that results in one or more of: (a) a reduction in the severity or duration of pain; (b) inhibition of pain; (c) a reduction or elimination of the use or need for analgesic therapy (e.g., opioids); (d) a reduction in the severity or duration of a symptom or an indication of cancer—e.g., a tumor lesion; (e) inhibition of tumor growth, or an increase in tumor necrosis, tumor shrinkage and/or tumor disappearance; (f) delay in tumor growth and development; (g) inhibition of tumor metastasis; (h) prevention of recurrence of tumor growth; (i) increase in survival of a patient with cancer pain; or (j) a reduction in the use or need for conventional anti-cancer therapy (e.g., elimination of need for surgery or reduced or eliminated use of chemotherapeutic or cytotoxic agents).

In certain embodiments, a therapeutically effective amount of the PD-1 inhibitor (e.g., an anti-PD-1 antibody or antigen-binding fragment thereof) can be from about 0.05 mg to about 1500 mg, from about 1 mg to about 1000 mg, from about 10 mg to about 850 mg, from about 50 mg to about 600 mg, from about 75 mg to about 400 mg, or from about 100 mg to about 350 mg of the antibody. For example, in various embodiments, the amount of the PD-1 inhibitor is about 0.05 mg, about 0.1 mg, about 1.0 mg, about 1.5 mg, about 2.0 mg, about 5 mg, about 10 mg, about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, or about 1500 mg.

The amount of a PD-1 inhibitor contained within an individual dose may be expressed in terms of milligrams of antibody per kilogram of subject body weight (i.e., mg/kg). In certain embodiments, the PD-1 inhibitor used in the methods disclosed herein may be administered to a subject at a dose of about 0.0001 to about 100 mg/kg of subject body weight. In certain embodiments, an anti-PD-1 antibody may be administered at dose of about 0.1 mg/kg to about 20 mg/kg of a patient's body weight. In certain embodiments, the methods of the present disclosure comprise administration of a PD-1 inhibitor (e.g., an anti-PD-1 antibody or antigen-binding fragment thereof) at a dose of about 1 mg/kg to 3 mg/kg, 1 mg/kg to 5 mg/kg, 1 mg/kg to 10 mg/kg, 1 mg/kg, 3 mg/kg, 5 mg/kg, or 10 mg/kg of a patient's body weight.

In certain embodiments, each dose comprises 0.1-10 mg/kg (e.g., 0.3 mg/kg, 1 mg/kg, 3 mg/kg, or 10 mg/kg) of the subject's body weight. In certain other embodiments, each dose comprises 5-600 mg of the PD-1 inhibitor (such as an anti-PD-1 antibody or antigen-binding fragment thereof), e.g., 5 mg, 10 mg, 15 mg, 20 mg, 25 mg, 30 mg, 40 mg, 45 mg, 50 mg, 100 mg, 150 mg, 200 mg, 250 mg, 300 mg, 400 mg, or 500 mg of the PD-1 inhibitor.

EXAMPLES

The following examples are put forth so as to provide those of ordinary skill in the art with a complete disclosure and description of how to make and use the methods and compositions of the present disclosure and are not intended to limit the scope of what the inventors regard as their invention. Likewise, the disclosure is not limited to any particular preferred embodiments described herein. Indeed, modifications and variations of the embodiments may be apparent to those skilled in the art upon reading this specification and can be made without departing from its spirit and scope. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Cemiplimab is a high-affinity, human, hinge-stabilized IgG4 monoclonal antibody to the PD-1 receptor that potently blocks the interactions of PD-1 with PD-L1 and PD-L2. Cemiplimab comprises a heavy chain having the amino acid sequence of SEQ ID NO: 9 and a light chain having the amino acid sequence of SEQ ID NO: 10; an HCVR/LCVR amino acid sequence pair comprising SEQ ID NOs: 1/2; and heavy and light chain CDR sequences (HCDR1, HCDR2, HCDR3, LCDR1, LCDR2, LCDR3) comprising SEQ ID NOs: 3-8, respectively, as described herein. See also U.S. Pat. No. 9,987,500.

Study Population

The study included 193 CSCC patients: 115 patients with metastatic CSCC (mCSCC), and 78 patients with locally advanced CSCC (laCSCC).

Inclusion Criteria: Patients who met the following criteria were eligible for inclusion in the study: adults with invasive CSCC not amenable to surgery or radiotherapy who also have ≥1 lesion, Eastern Cooperative Oncology Group (ECOG) performance status ≤1, and life expectancy >12 weeks.

Demographic characteristics were generally similar across the treatment groups, as summarized in Table 1. Most patients were male (n=161, 83.4%), with a median age of 72.0 (range, 38-96) years. Most patients had a primary cancer site of head and neck (n=131, 67.9%). Median duration of follow-up was 15.7 months (range: 0.6-36.1) among all patients; with 18.5 months (range: 1.1-36.1) for Group 1, 15.5 months (range: 0.8-35.6) for Group 2, and 17.3 months (range: 0.6-26.3) for Group 3. The median duration of exposure was 51.1 weeks (range, 2.0-109.3) and the median number of doses was 18 (range, 1-48). Number of patients with cemiplimab as first-line therapy was 128 (66.3%). Number of patients with prior systemic therapy was 65 (33.7%).

TABLE 1

Patient Demographics and Clinical Characteristics

| Variable | Total (N = 193) | mCSCC 350 mg Q3W (n = 56) | mCSCC 3 mg/kg Q2W (n = 59) | laCSCC 3 mg/kg Q2W (n = 78) |
|---|---|---|---|---|
| Age, mean ± SD, years | 71.1 ± 11.4 | 69.7 ± 12.8 | 70.4 ± 10.1 | 72.5 ± 11.2 |
| ≥65 years, n (%) | 144 (74.6) | 42 (75.0) | 43 (72.9) | 59 (75.6) |
| Male, n (%) | 161 (83.4) | 48 (85.7) | 54 (91.5) | 59 (75.6) |
| ECOG, n (%) | | | | |
| 0 | 86 (44.6) | 25 (44.6) | 23 (39.0) | 38 (48.7) |
| 1 | 107 (55.4) | 31 (65.4) | 36 (61.0) | 40 (51.3) |
| Primary site | | | | |
| Head and neck | 131 (67.9) | 31 (55.4) | 38 (64.4) | 62 (79.5) |
| Other | 62 (32.1) | 25 (44.6) | 21 (35.6) | 16 (20.5) |
| Prior cancer-related systemic therapy, n (%) | 65 (33.7) | 20 (35.7) | 33 (65.9) | 12 (15.4) |
| Prior cancer-related radiotherapy, n (%) | 131 (67.9) | 38 (67.9) | 50 (84.7) | 43 (55.1) |

SD, standard deviation.

Example 1: Clinical Trial of Cemiplimab in Patients with Advanced CSCC

This example describes a phase 2, non-randomized, single-arm, global, clinical trial of cemiplimab administered to adult patients with invasive CSCC not amenable to surgery or radiotherapy. Results of this trial confirm the association between time to meaningful reduction in pain and tumor response.

Study Treatment

Open-label cemiplimab was supplied as a liquid in sterile, single-use vials. Each vial contained cemiplimab at a concentration of 50 mg/mL. Patients (N=193) received intravenous (IV) cemiplimab 3 mg/kg every 2 weeks (Q2W) (mCSCC n=59; Group 1); laCSCC n=78; Group 2)) for 12 treatment cycles or 350 mg every 3 weeks (Q3W) (mCSCC n=56; Group 3) for six treatment cycles.

The primary efficacy endpoint was objective response rate, defined as the proportion of patients with complete or partial response.

Complete Response (CR): Disappearance of all target lesions. Any pathological lymph nodes (whether target or non target) must have reduction in short axis to <10 mm (<1 cm).

Partial Response (PR): At least a 30% decrease in the sum of the diameters of target lesions, taking as reference the baseline sum diameters.

Data was collected regarding duration of response (DOR) and health-related quality of life (HRQoL).

Pain Analysis

The European Organization for Research and Treatment of Cancer (EORTC) cancer specific 30-item questionnaire (QLQ-C30) quality of life scale was administered to patients at baseline and on day 1 of each treatment cycle.

The QLQ-C30 includes a symptom subscale that specifically evaluates pain with a score range 0-100. Lower scores indicate less pain.

The QLQ-C30 also includes five function domains (physical, emotional, social, role and cognitive), seven other symptoms (fatigue, nausea/vomiting, constipation, diarrhoea, insomnia, dyspnoea and appetite loss), as well as global health status/health-related quality of life and financial difficulties (Aaronson et al., *J Natl Cancer Inst.* 1993; 85:365-376). Participants respond on a four-point scale from "not at all" to "very much" and items use a "past week" recall period. Raw scores on all scales are linearly converted to a 0-100 scale with higher scores reflecting higher levels of function and higher levels of symptom burden.

Mixed effects repeated measures models were used to assess the significance of changes from baseline in pain score in patients who had baseline and post-baseline assessments. The model included fixed effects of treatment, visit, treatment-by-visit interaction and baseline value of the pain score. Results were expressed as the least squares (LS) mean and standard error (SE).

A clinically meaningful change from baseline in pain was defined as a change in pain score ≥10 points on the QLQ-C30 (Osoba et al., *J Clin Oncol.* 1998; 16:139-144). This threshold for a within patient change was determined using a distribution-based method that considered an effect size of 0.5 (McLeod et al., *Expert Rev Pharmacoecon Outcomes Res.* 2011; 11:163-169; Revicki et al., *J Clin Epidemiol.* 2008; 61:102-109).

Kaplan-Meier (KM) survival analysis (with censoring at drop-out) was used to estimate time to first clinically meaningful reduction (improvement) or increase (deterioration) in QLQ-C30 pain score in patients who had baseline pain scores that allowed for at least a 10-point change. Concomitant pain medication usage (dose, starting and end days) data were collected during the study using the Anatomical Therapeutic Chemical (ATC) classification. Opioids, in particular, were analyzed at each treatment-cycle evaluation point, adjusted for duration to calculate cumulative number of days on opioids per patient-year, using Poisson regression with the treatment group as fixed factors and patients' treatment exposure duration as offset variable.

Time to Clinical Response

Clinical responders were defined by Response Evaluation Criteria In Solid Tumors (RECIST) complete+partial tumor response (objective response rate). Clinical non-responders were those with stable or progressive disease. KM analysis was used to determine the time to clinical response and progression-free survival (PFS).

Results

As shown in FIG. 1, statistically significant and clinically meaningful reductions in pain were observed among patients who had both baseline and post-baseline pain assessments. The horizontal broken line indicates the threshold for a clinically meaningful change. A significant reduction in pain score was observed as early as cycle 2, and by cycle 3, the improvement was also clinically meaningful (≥10 points). Further improvements were observed subsequent to cycle 3 and were maintained until cycle 12.

Clinical responders reported a clinically meaningful reduction in pain from baseline as early as cycle 2 (P<0.0001), in contrast to clinical non-responders (FIG. 1). Among these clinical responders, there was further pain reduction that was sustained with successive treatment cycles. In contrast, changes from baseline among clinical non-responders showed large fluctuations that were neither statistically significant nor clinically meaningful.

Figure 2:
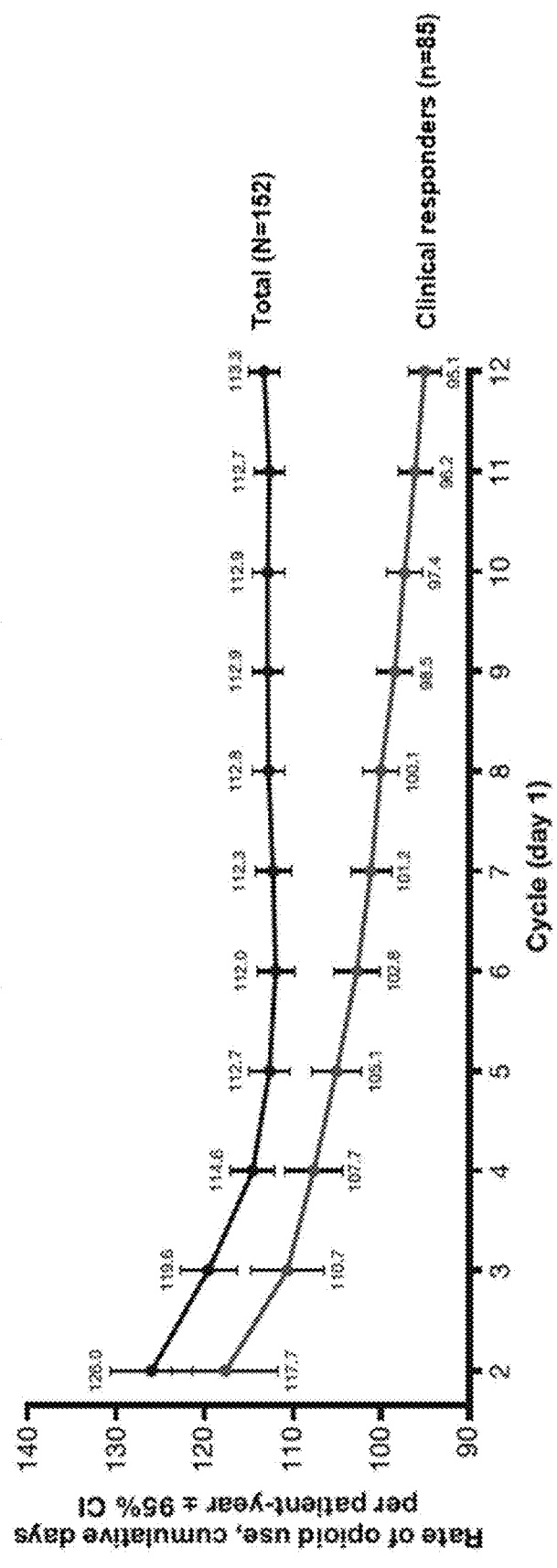
FIG. 2 shows cumulative number of days on opioids over time among patients who had baseline and post-baseline assessment of the QLQ-C30 pain scale, in connection with the study described in Example 1 herein.

As shown in FIG. 2, pain reduction in the total population and among clinical responders was independent of opioid pain medication use. The cumulative number of days on opioids among clinical responders showed a steady reduction in the rate of opioid use with increasing cycles of cemiplimab treatment.

The relationship between clinically meaningful changes in pain and clinical response among patients with CSCC treated with cemiplimab is summarized in Table 3. The "n" values reflect the number of patients who had baseline and post-baseline assessment scores on the QLQ-C30 pain scale.

TABLE 2

Relationship between changes in pain and clinical response

|  | Clinical responders (complete + partial) | Clinical non-responders (stable + progressive) | All |
|---|---|---|---|
| Baseline pain score, mean ± SD (n) | 26.5 ± 29.1 (85) | 33.7 ± 31.1 (83) | 30.1 ± 80.3 (168) |
| Change from baseline in pain score at first tumour response, n | 85 | 67 | — |
| LS mean change ± SE | −15.2 ± 1.5† | −3.9 ± 2.1 | — |
| LS mean (95% CI) difference vs non-responders | −11.3 (−16.3, −6.3)‡ | — | — |
| Median time to clinical response, months (n) | 2.0 (85) | — | — |
| Median PFS, months (n) | — | — | 18.4 (193) |
| Median time to first pain improvement, months (n) | 2.1 (51) | — | 2.1 (100) |

TABLE 2-continued

Relationship between changes in pain and clinical response

|  | Clinical responders (complete + partial) | Clinical non-responders (stable + progressive) | All |
|---|---|---|---|
| Median time to first pain deterioration, months (n) | 20.6 (80) | — | 14.8 (142) |

[†]P < 0.0001 relative to baseline;
[‡]P < 0.0001 compared with non-responders.

Figure 3A:
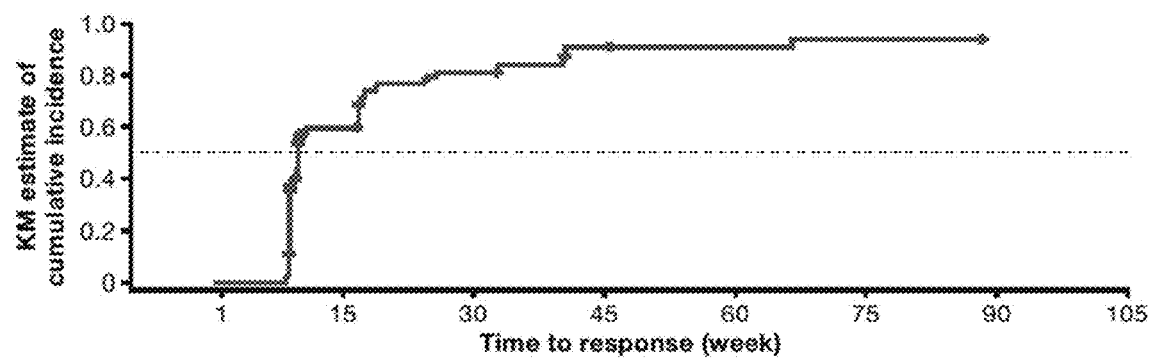
FIG. 3A shows Kaplan-Meier (KM) survival analysis of time to first clinically meaningful improvement in pain score in patients assessed in the study described in Example 1 herein.
Figure 3B:
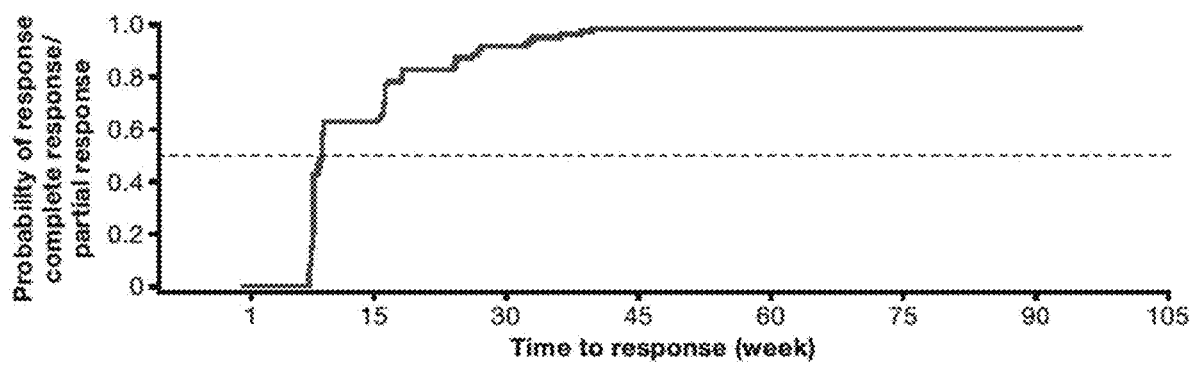
FIG. 3B shows KM survival analysis of time to first tumor response in patients assessed in the study described in Example 1 herein.

The median time to first clinically meaningful pain improvement in all patients was 2.1 months, and approximated the median time to first tumor response of 2.0 months that was estimated for clinical responders (Table 2). These results are also depicted in FIG. 3A, which shows the time to clinically meaningful pain improvement, and FIG. 3B, which shows the time to first tumor response. In FIGS. 3A and 3B, the time point where the horizontal broken line (50% survival probability) crosses the curve indicates the median time to response.

Among clinical responders, the median time to first clinically meaningful pain improvement was 2.1 months. The LS mean (SE) change from baseline in pain score at first tumor response was −15.2 (1.5) among responders and −3.9 (2.1) among non-responders, resulting in a statistically and clinically meaningful LS mean (95% CI) difference of −11.3 (−16.3, −6.3; P<0.0001).

Figure 4A:
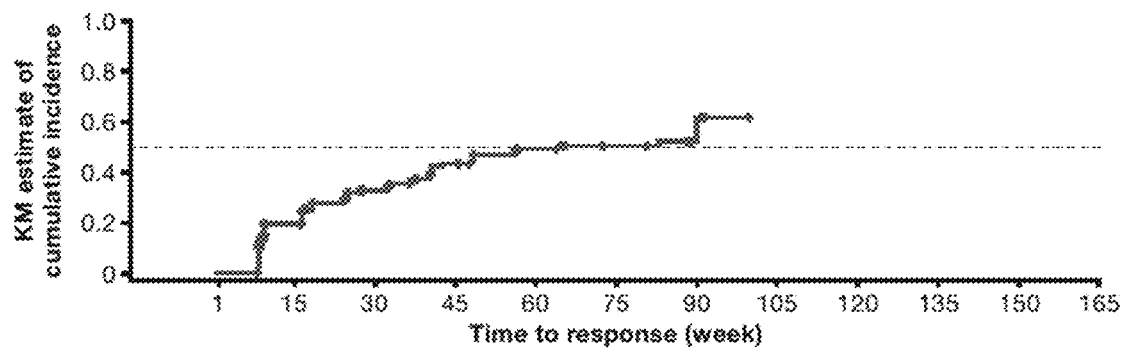
FIG. 4A shows KM survival analysis of time to first clinically meaningful deterioration in pain score in patients assessed in the study described in Example 1 herein.
Figure 4B:
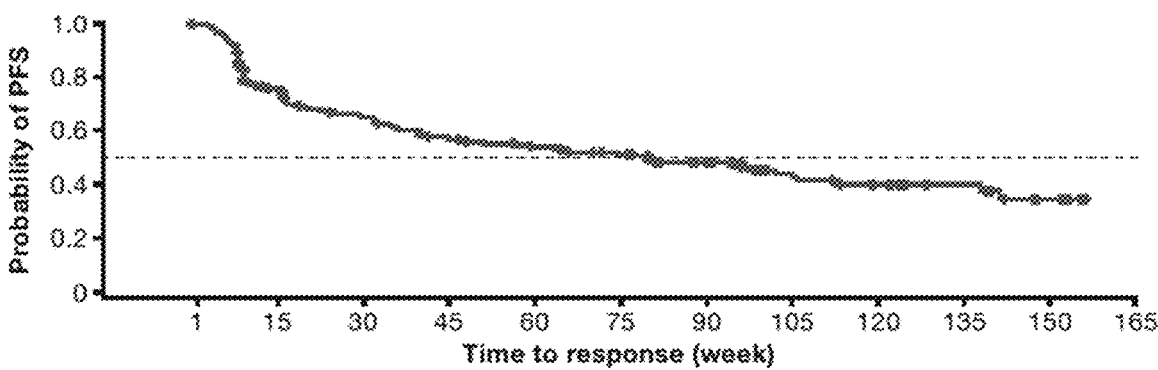
FIG. 4B shows KM survival analysis of time to progression-free survival (PFS) in patients assessed in the study described in Example 1 herein.

The median time to first clinically meaningful deterioration in pain, 14.8 months, approximated the median time to progression-free survival (PFS) of 18.4 months (Table 2). These results are also depicted in FIG. 4A, which shows the time to first clinically meaningful deterioration in pain score, and FIG. 4B, which shows the time to PFS. Among clinical responders, the median time to first clinically meaningful pain deterioration was 20.6 months (Table 2). In FIGS. 4A and 4B, the time point where the horizontal broken line (50% survival probability) crosses the curve indicates the median time to response.

Overall response rate (ORR) was 46.1% (95% CI: 38.9-53.4); overall, 16.1% of patients achieved CR (Table 3). ORR was 50.8% (95% CI: 37.5-64.1) for Group 1, 44.9% (95% CI: 33.6-56.6) for Group 2, and 42.9% (95% CI: 29.7-56.8) for Group 3. ORR was 48.4% in patients who had not received prior anticancer systemic therapy (n=128) and 41.5% among those who had received prior anticancer systemic therapy (n=65).

DCR, durable DCR, median DOR and KM 12-month estimate of DOR, are provided in Table 3. With 1-year additional follow-up, the median DOR was not reached (observed DOR range: 1.9-34.3 months). In responding patients, the estimated proportion of patients with ongoing response at 12 months was 87.8% (95% CI: 78.5-93.3). Estimated median PFS was 18.4 months (95% CI: 10.3-24.3) for all patients. The KM estimated progression-free probability at 24 months was 44.2% (95% CI: 36.1-52.1). The KM estimated probability of OS at 24 months was 73.3% (95% CI: 66.1-79.2).

TABLE 3

Tumor Response to Cemiplimab

|  | Group 1 (mCSSC) 3 mg/kg Q2W (n = 59) | Group 2 3 mg/kg Q2W (laCSCC) (n = 78) | Group 3 (mCSCC) 350 mg Q3W (n =56) | Total (N = 193) |
|---|---|---|---|---|
| Median duration of follow-up. months (range) | 18.5 (1.1-36.1) | 15.5 (0.8-35.6) | 17.3 (0.6-26.3) | 15.7 (0.6-36.1) |
| Overall response (95% CI) | 50.8 (37.5-64.1) | 44.9 (33.6-56.6) | 42.9 (29.7-56.8) | 46.1 (38.9-53.4) |
| Best overall response, n (%) |  |  |  |  |
| Complete response | 12 (20.3) | 10 (12.8) | 9 (16.1) | 31 (16.1) |
| Partial response | 18 (30.5) | 25 (32.1) | 15 (26.8) | 58 (30.1) |
| Stable disease | 9 (15.3) | 27 (34.6) | 10 (17.9) | 46 (23.8) |
| Non-complete response/non-progressive disease | 3 (5.1) | 0 | 2 (3.6) | 5 (2.6) |
| Progressive disease | 10 (16.9) | 10 (12.6) | 14 (25.0) | 34 (17.6) |
| Not evaluable | 7 (11.9) | 6 (7.7) | 6 (10.7) | 19 (9.8) |
| DCR, % (95% CI) | 712 (57.9-82.2) | 79.5 (68.8-87.8) | 64.3 (50.4-76.6) | 72.5 (65.7-78.7) |
| Durable DCR[†], % (95% CI) | 61.0 (47.4-73.5) | 62.8 (51.1-73.5) | 57.1 (43.2-70.3) | 60.6 (53.3-67.6) |
| Median observed time to response, months (IQR)[‡] | 1.9 (1.8-2.0) | 21 (1.9-3.8) | 2.1 (2.1-4.2) | 2.1 (1.9-3.7) |
| Median observed time to complete response, months (IQRY | 11.1 (7.5-18.4) | 10.5 (7.4-12.9) | 12.4 (8.2-16.6) | 11.2 (7.4-14.8) |
| Kaplan-Meier estimated median DOR, months (95% CI)[‡] | NR (20.7, NE) | NR (18.4, NE) | NR (NE, NE) | NR (28.8, NE) |
| Kaplan-Meier 12-month estimate of DOR, % (95% CI) | 89.5 (70.9-96.5) | 83.2 (64.1-92.7) | 91.7 (70.6-97.8) | 87.8 (78.5-93.3) |

Complete response (CR) rates were 20.3%, 12.8%, and 16.1% for Groups 1, 2 and 3, respectively. Median time to CR was 11.2 months. The estimated proportion of patients with ongoing response at 12 months was 87.8% (95% CI: 78.5-93.3), with median DOR not reached. KM estimated probability of overall survival (OS) was 73.3% (95% CI: 66.1-79.2) at 24 months, with median OS not reached. Global health status/HRQoL improvements were observed as early as 4 months. The KM estimate of median time to first clinically meaningful improvement for pain was 2.1 (95% CI: 2.0-3.7) months overall. No new safety concerns were observed.

Health-Related Quality of Life: Baseline scores for QLQ-C30 indicated generally moderate-to-high levels of functioning and moderate-to-low symptom burden. For global health status/HRQoL, improvements were observed from 4 months, with statistically significant improvement from baseline observed at 6 months (least squares (LS) mean [standard error (SE)] change 7.8 [1.6]; P<0.0001). Improvements in global health status/HRQoL had reached the clinically meaningful threshold (≥10-point change) by 24 months (LS mean [SE] change 11.1 [2.6]; P<0.0001). Among the functional scales, significant improvements were observed in emotional function and social function scales at 6 months and 24 months. Physical function, role function, and cognitive function did not deteriorate and remained stable relative to baseline. With regards to symptoms, significant improvements from baseline were also observed for symptoms of pain, insomnia, appetite loss, and constipation by 6 months, and as early as 4 months for pain. These symptoms had all reached the clinically meaningful threshold (≥10 points change) by 24 months. Across all functional scales and symptom scales, the proportion of patients with clinically meaningful deterioration was generally low at both 6 and 24 months.

Figure 5:
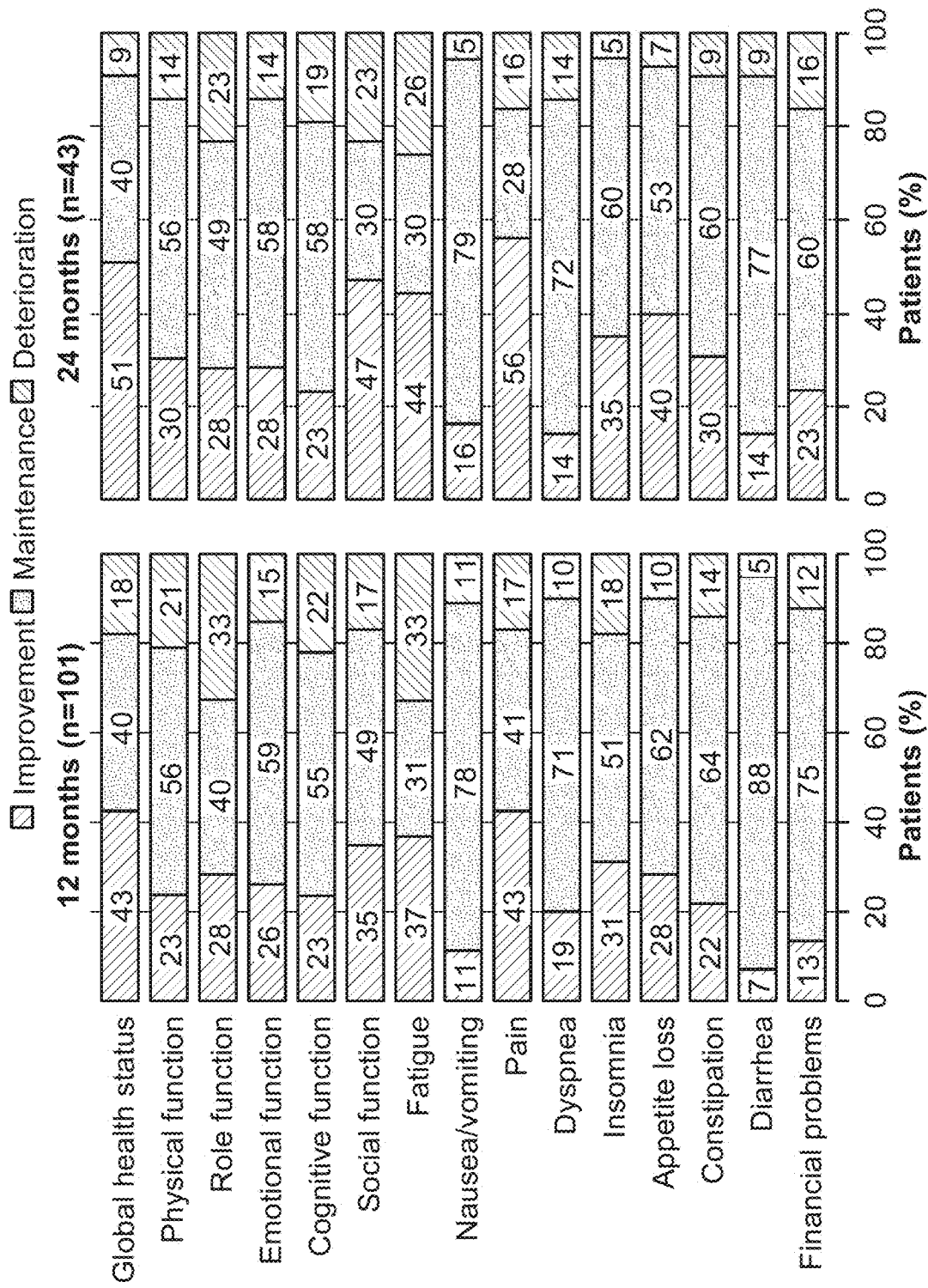
FIG. 5 shows the proportion of patients reporting clinically meaningful change in global health status/HRQoL, functional scales, and symptom in the study described in Example 1 herein.

By 12 months, among all patients reporting clinically meaningful change (≥10-point change), most patients experienced clinically meaningful improvements or stability in global health status/HRQoL (83%), functional scales (68-85%), and symptoms (68-95%) (FIG. 5). Overall, 91% of responders experienced clinically meaningful improvement or stability in global health status/HRQoL scores at 24 months and the majority of patients showed sustained improvement and stabilization across all functional scales (77-86%) and symptoms (74-95%) by 24 months. The proportions of patients with clinically meaningful deterioration in functional scales were generally low at both evaluated time points.

Conclusions

In cemiplimab-treated CSCC patients, early and rapid pain reduction was observed, and approximated time to first tumor response (2 months). Improvements in pain were clinically meaningful and sustained at subsequent cycles of treatment. Clinically meaningful deterioration in pain (i.e., worsening) approximated PFS. These results show that changes in pain correlate with clinical tumor response.

Patients with advanced CSCC receiving cemiplimab had deepening responses over time, evidenced by increasing CR rates compared to primary analyses. Clinical responses to cemiplimab also led to measurable improvements in QoL. These updated DOR and CR results provide further evidence that the efficacy of cemiplimab against advanced CSCC surpasses that observed for other immune checkpoint inhibitors for any advanced solid tumor type.

Example 2: Clinical Trial of Cemiplimab in Patients with Locally Advanced Basal Cell Carcinoma (laBCC)

While BCC is generally treated surgically or with other local modalities, a small proportion of patients develop laBCC and require systemic therapy such as with hedgehog signaling pathway inhibitors (HHIs). However, intolerance and resistance to HHIs are common. Patients with BCC report disease-related symptoms, including pain, adversely affect health-related quality of life (QoL), daily function, and emotional well-being. Cemiplimab-rwlc is the first immunotherapy to receive full approval in the US for patients with laBCC and accelerated approval for metastatic BCC, post-HHI, or for whom HHIs are not appropriate.

This example describes a phase 2 clinical trial of cemiplimab administered to adult patients with laBCC who progressed on or were intolerant to hedgehog inhibitor (HHI) therapy (NCT03132636). Overall response rate (complete+partial) was 31.0% and 48.8% had stable disease. Health-related Quality of Life (QoL) was evaluated in these patients because QoL is impaired in patients with laBCC. Patient-reported health-related QoL was a pre-defined secondary endpoint in the clinical trial. Results of this trial confirm clinically meaningful improvement of pain in laBCC patients.

Methods

For inclusion in this Phase II, single-arm, multicenter, pivotal trial of cemiplimab, patients were required to be adults (≥18 years) with histologically confirmed diagnosis of BCC, Eastern Cooperative Oncology Group (ECOG) performance status 51, and not candidates for further HHI therapy due to disease progression or intolerance to prior HHI therapy or have no better than stable disease after 9 months on HHI therapy.

Patients received IV cemiplimab 350 mg every 3 weeks (Q3W) for up to 9 treatment cycles. At baseline (BL) and day 1 of each cycle (C), patients completed EORTC QLQ-C30 (Aaronson et al., *J Natl Cancer Inst*, 1993; 85:365-376) and SKINDEX-16 (Chren et al., *J Cutan Med Surg.*, 2001; 5:105-110) questionnaires that assess Global Health Status (GHS)/QoL, functioning, and laBCC symptoms (Bottomley et al., *Eur J Cancer*, 2005; 41(12):1697-709; Atherton et al., *Support Care Cancer*, 2012 August; 20(8): 1729-1735). QLQ-C30 scores range from 0 to 100, with higher scores on the GHS/QoL scale and functional domains indicative of better outcomes, and lower symptom scores indicative of better outcomes. On SKINDEX-16, lower scores indicate less disease impact on the three subscales assessing emotions, functioning and symptoms. A change of at least 10 points was considered clinically meaningful on QLQ-C30 and SKINDEX-16. Follow-up assessment was conducted 28 to 42 days after the last study treatment administration if a patient discontinued early.

Analyses were conducted on the full analysis set, which consisted of all enrolled patients who were deemed eligible for the study. Mixed-model repeated measures (MMRM) analysis was used to estimate least squares (LS) mean (standard error [SE]) change from BL during treatment (i.e., across C2 to C9) on all scales for patients with baseline and at least one post-baseline value. On each of QLQ-C30 and SKINDEX-16, changes of ≥|10|points were considered clinically meaningful in these models. Responder analyses were conducted in patients with non-missing data from BL to determine the proportions with clinically meaningful improvement or deterioration, or maintenance from baseline (stability) on QLQ-C30 and SKINDEX-16 at C2 and C9; a threshold of 10 points was considered meaningful for both instruments. Maintenance was defined as neither improvement nor deterioration that was clinically meaningful.

Results

A total of 84 patients with laBCC were enrolled in the study with a median age of 70 years old (Table 4). The head and neck region was the primary tumor site in the majority of patients (89.3%); and 60% of patients had ECOG of 0.

TABLE 4

Patient characteristics at baseline (N = 84)

| Variable | Value |
| --- | --- |
| Age, median (IQR), years | 70 (61-79) |
| ≥65 years, n (%) | 53 (63.1) |
| Male sex, n (%) | 56 (66.7) |
| ECOG performance status score, n (%) | |
| 0 | 51 (60.7) |
| 1 | 33 (39.3) |
| Prior therapy, n (%) | |
| Cancer-related radiotherapy | 42 (50.0) |
| HHI therapy* | |
| Vismodegib | 79 (94.0) |
| Sonidegib | 14 (16.7) |
| Vismodegib + sonidegib | 9 (10.7) |
| Reason for discontinuation of prior HHI, n (%)* | |
| Disease progression | 60 (71.4) |
| Intolerance | 32 (38.1) |
| Intolerant to vismodegib | 32 (38.1) |
| Intolerant to sonidegib | 4 (4.8) |
| No better than stable disease after 9 months on HHI | 7 (8.3) |
| Primary BCC site, n (%) | |
| Head and neck | 75 (89.3) |
| Trunk | 7 (8.3) |
| Extremity | 2 (2.4) |

IQR, interquartile range.

*Sum is >84 because of patient overlap among categories.

Figures 6A, 6B:
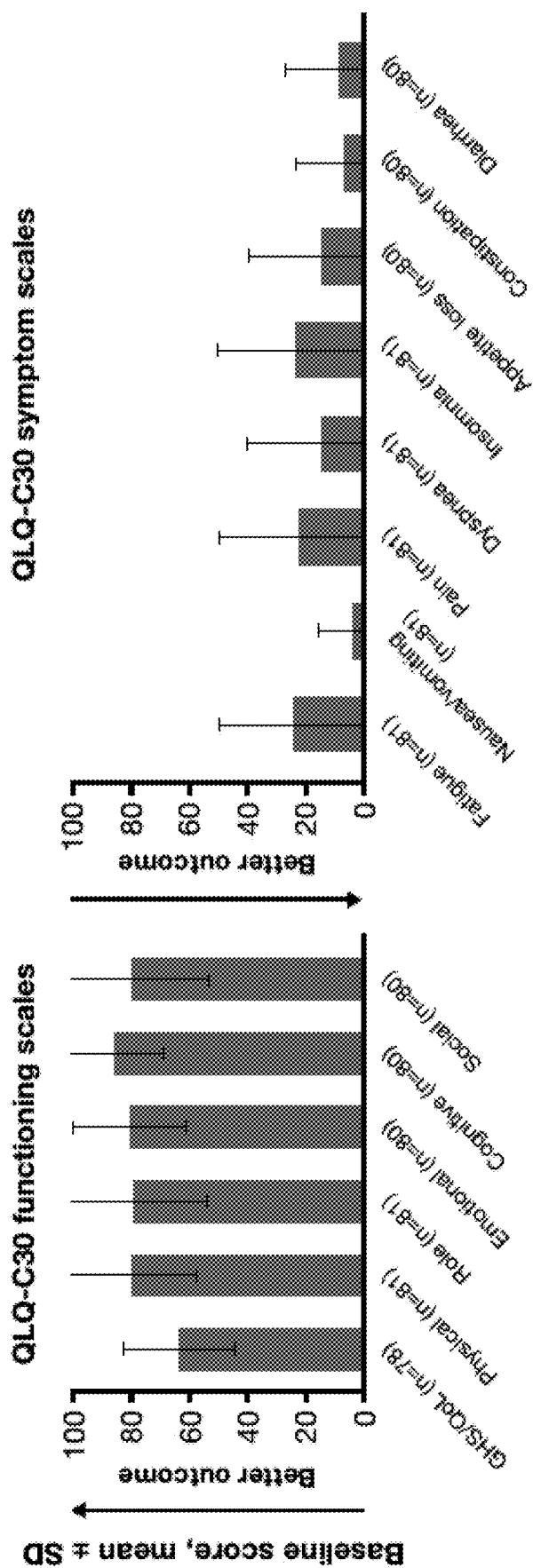
FIGS. 6A-6D show baseline scores and overall change from baseline (MMRM) on the QLQ-C30 in patients in the full analysis set who had baseline and at least one post-baseline value in the study described in Example 2 herein.
Figures 6C, 6D:
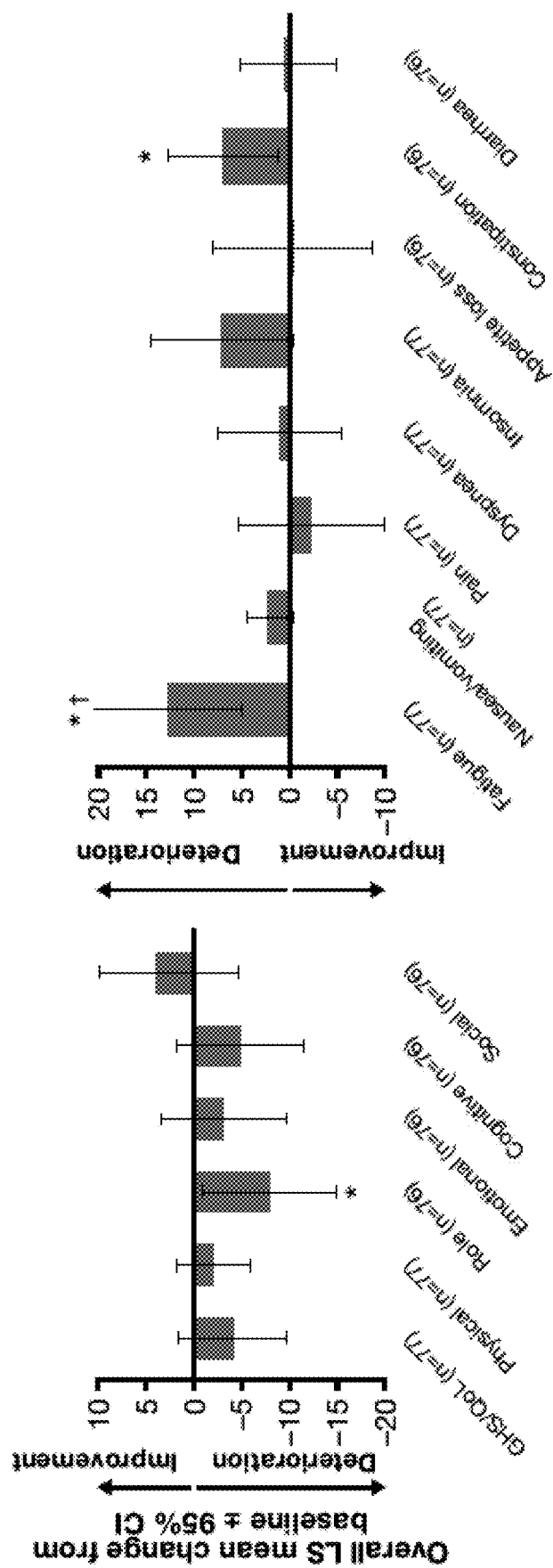

Baseline QLQ-C30 scores showed moderate to high levels of functioning and low symptom burden (FIGS. 6A, 6B). In the MMRM analyses, changes from baseline over the full study period showed maintenance for GHS/QoL and all other scales (change <10 points) except for worsening of fatigue (LS mean [SE] change 12.5 [3.9]; P<0.05) (FIGS. 6C, 6D).

Figure 7:
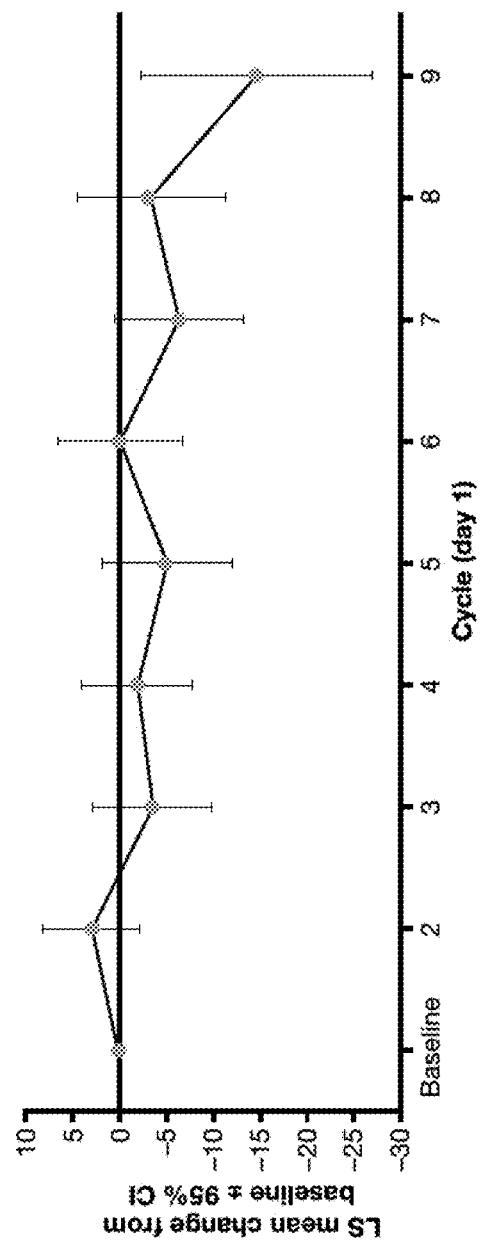
FIG. 7 shows MMRM analysis of change from baseline by treatment cycle in patients in the full analysis set who had baseline and at least one-post baseline value in the study described in Example 2 herein.

Change in QLQ-C30 GHS/QoL scores also suggested that overall health-related QoL was generally maintained across the study duration (FIG. 7).

Figure 8:
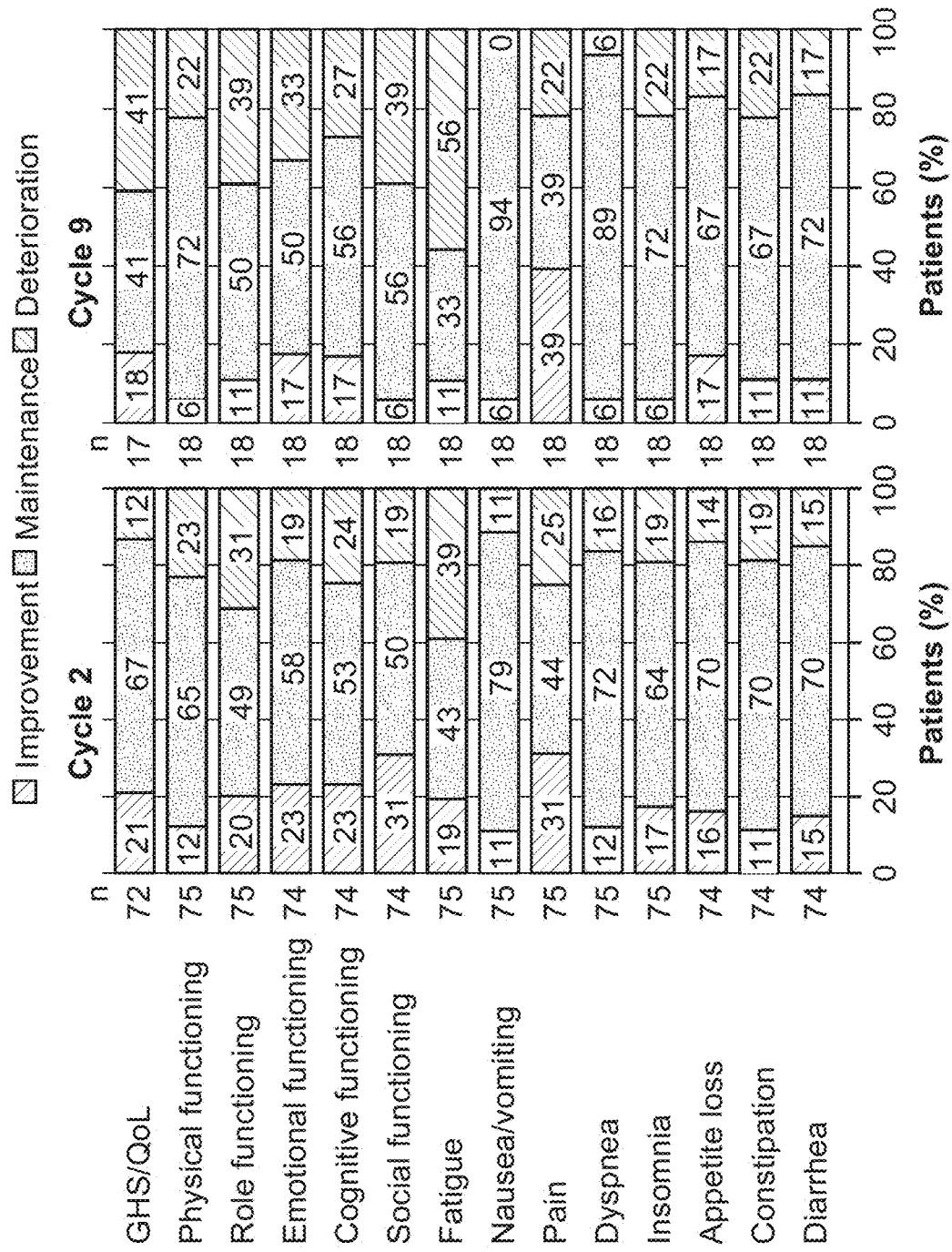
FIG. 8 shows the proportion of patients reporting clinically meaningful improvement, clinically meaningful deterioration, or maintenance on the QLQ-C30 at cycles 2 and 9 in the study described in Example 2 herein.

In responder analysis, the majority of patients reported clinically meaningful improvement or maintenance at C2 on all functioning and symptom scales (FIG. 8). On the key symptom of pain, 31% of patients reported a clinically meaningful improvement and 44% reported maintenance. Results at C9 were generally consistent with what was observed at C2; the majority of patients reported clinically meaningful improvements or maintenance on all QLQ-C30 functioning scales and the key symptom of pain, but not fatigue (FIG. 8).

Figure 9A:
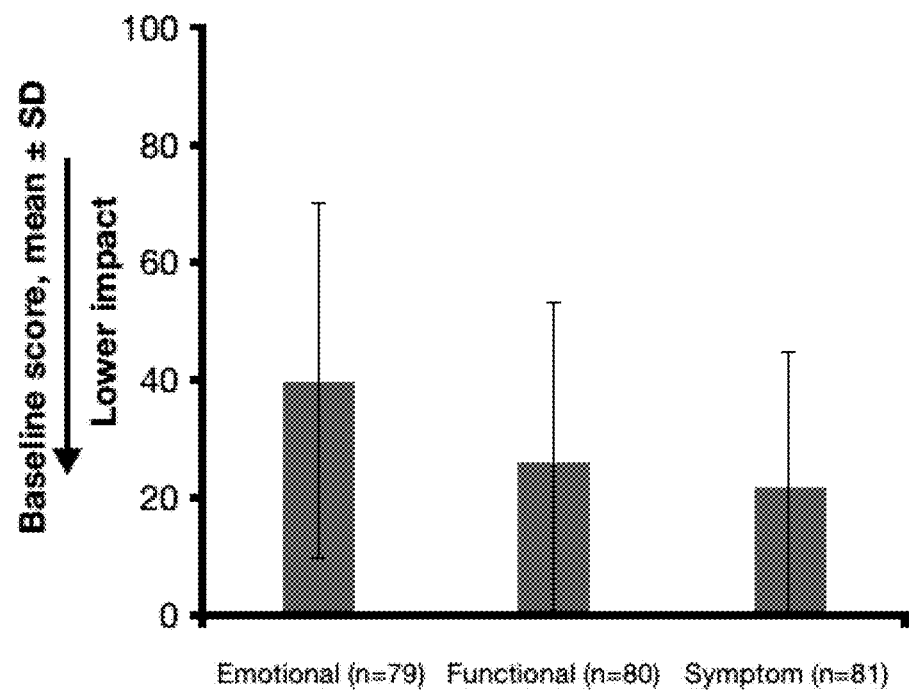
FIG. 9A shows baseline scores and FIG. 9B shows overall change from baseline (MMRM) in patients in the full analysis set who had baseline and at least one post-baseline assessment on SKINDEX-16 subscales in the study described in Example 2 herein. *P<0.05 vs baseline; †Clinically meaningful change.
Figure 9B:
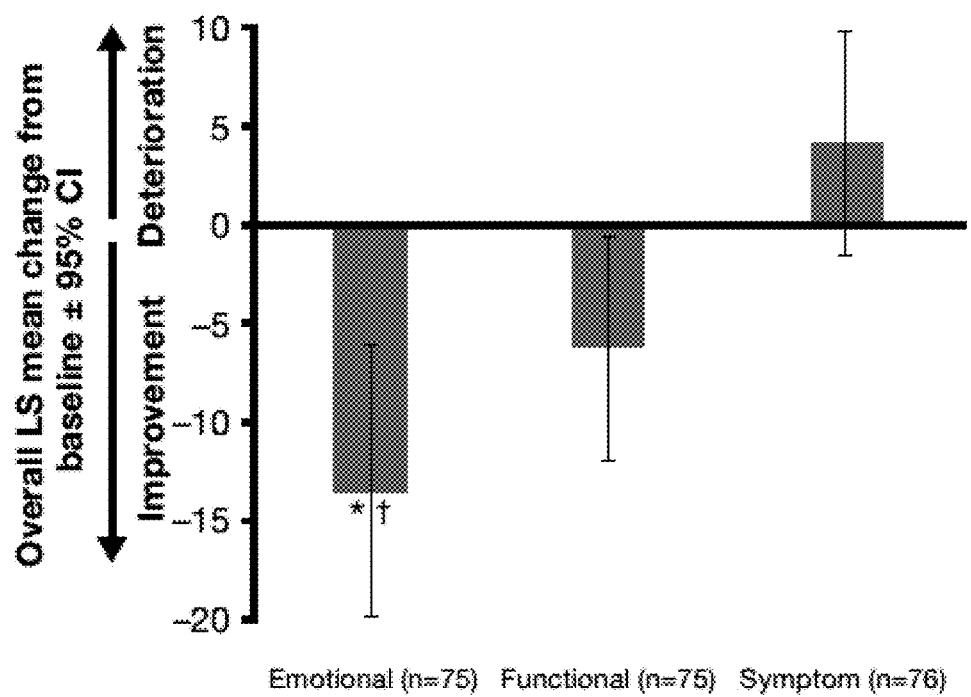
Figure 10:
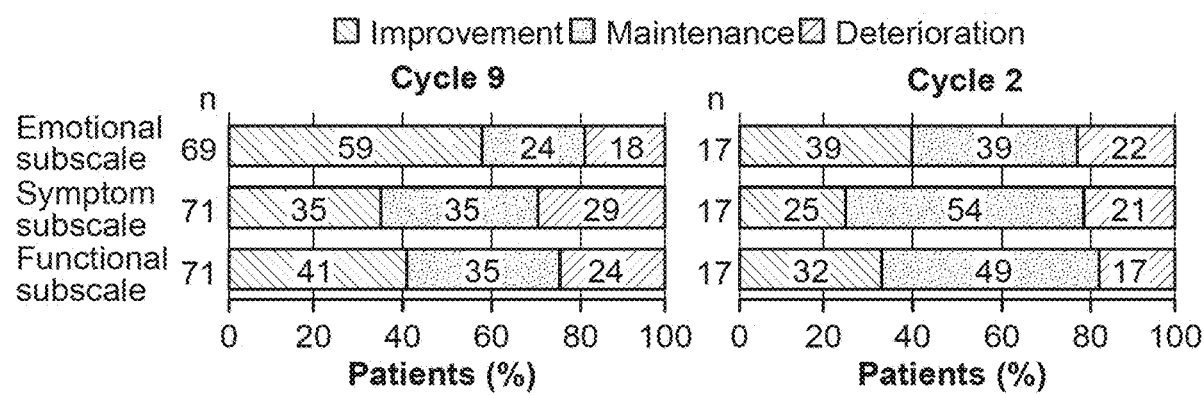
FIG. 10 shows proportion of patients reporting clinically meaningful improvement, clinically meaningful deterioration, or maintenance on the SKINDEX-16 at cycles 2 and 9 in the study described in Example 2 herein.

On the SKINDEX-16, MMRM analyses showed clinically meaningful improvement in the overall change from baseline on the emotional subscale (LS mean [SE] change −13.2 [3.9]; P<0.05), and maintenance on the symptom and functional subscales (FIGS. 9A, 9B). Responder analysis showed the majority of patients reported clinically meaningful improvements or maintenance at C2 across the SKINDEX-16 subscales (FIG. 10). Similar results were observed at C9 with 70-80% of patients reporting clinically meaningful improvement or maintenance (FIG. 10).

Conclusions

Patients had high levels of function and low symptom burden at baseline. This pivotal clinical trial of cemiplimab showed that in addition to providing substantial anti-tumor activity in patients with laBCC in the second-line setting, cemiplimab resulted in significant improvement or maintenance in overall health-related QoL and functioning for the majority of patients. On the SKINDEX-16 emotional scale in particular, nearly 60% of patients reported clinically meaningful improvement with cemiplimab. Patients also reported maintenance of a low symptom burden except for fatigue. Despite the high presence of fatigue, functional status was maintained over the full study period.

Example 3: Follow Up Analysis of Cemiplimab in Patients with Advanced CSCC

This example relates to the phase 2 clinical trial of cemiplimab in advanced CSCC, as described in Example 1, and provides pooled longer-term data from the three groups of patients included in the study: Group 1 (mCSCC patients who received 3 mg/kg Q2W IV for up to 96 weeks, n=59); Group 2 (laCSCC patients who received 3 mg/kg Q2W IV for up to 96 weeks, n=78); and Group 3 (mCSCC patients who received 350 mg Q3W IV for up to 54 weeks, n=56).

In primary analyses of the phase 2 data (NCT02760498), Group 1 and Group 2 exhibited substantial antitumor activity, emerging evidence of durable response, and an acceptable safety profile (Migden et al., 2020; Migden et al., 2018); and the primary analysis of Group 3 and 11 months follow-up data of Group 1 showed similar activity (Rischin et al., 2020). The additional pooled data from Groups 1, 2, and 3 provided in this example include updated duration of response (DOR) and complete response (CR) rates, as well as the impact of cemiplimab on durability of pain control and QoL.

Background

CSCC is the second most common skin cancer in the US, with increasing incidence (Que et al., 2018). Most cases are cured by complete surgical excision. (Cranmer et al., 2010; National Comprehensive Cancer Network, 2020). However, a small but substantial number of patients present with or subsequently develop mCSCC or laCSCC not amenable to curative surgery or curative radiation (collectively, "advanced CSCC"), which has a poor prognosis (Karia et al., 2014; Weinberg et al., 2007; Schmults et al., 2013).

Treatment of advanced CSCC, particularly CSCC with a primary site of head and neck, can lead to reduced quality of life (QoL) (Arunachalam et al., 2011; Katz et al., 2003; Rhee et al., 2005). Surgery for CSCC can result in considerable morbidity, for example, some patients require orbital exenteration (Gerring et al., 2017), which significantly reduces QoL, including increased anxiety and depression, difficulty driving, phantom pain, and hallucinations (Ye et al., 2015; Kondo et al., 2013). Radiotherapy is associated with substantial toxicity, including fibrosis, lymphedema, skin necrosis, and functional deficits (Brook et al., 2020; Stratigos et al., 2015). Furthermore, pain is a common symptom associated with detriments to QoL, especially among those with CSCC for which curative surgery is not an option (Mills et al., 2012).

Assessments

The primary efficacy endpoint was ORR. Secondary endpoints included DOR, PFS, OS, CR rate, safety and tolerability, and QoL. Durable disease control rate (DCR), defined as the proportion of patients with response or stable disease 105 days, was examined. An exploratory clinical activity analysis by prior systemic therapy was performed.

The EORTC Quality of Life Questionnaire Core 30 (QLQ-C30) (Aaronson et al., 1993) was used to evaluate impact of cemiplimab on symptoms and functioning. The QLQ-C30 includes GHS/QoL, financial impact, functioning domains (physical, emotional, social, role, and cognitive), and symptoms (pain, fatigue, nausea/vomiting, constipation, diarrhea, insomnia, dyspnea, and appetite loss). For GHS/QoL, this scale includes two questions ('how would you rate your overall health?' and 'how would you rate your overall QoL?'). Participants respond on a four-point scale from "not at all" to "very much" for impact of each scale over the past week, with raw scores on all scales linearly converted to a 0-100 scale (higher scores reflect higher levels of functioning and higher levels of symptom burden). The questionnaire was administered on day 1 of each treatment cycle (treatment cycle defined as 8 weeks for Groups 1 and 2 and 9 weeks for Group 3). Analysis included longitudinal effects of cemiplimab on GHS/QoL, functioning status, and symptoms, including pain. Assessment per cycle or time were similar and thus are reported in cycles. Analyses of time to first clinically meaningful improvement for pain and time to first clinically meaningful deterioration for pain were also performed. Safety assessments included treatment-emergent adverse events (TEAEs), laboratory tests, vital signs, and physical examinations.

Results

Figure 11:
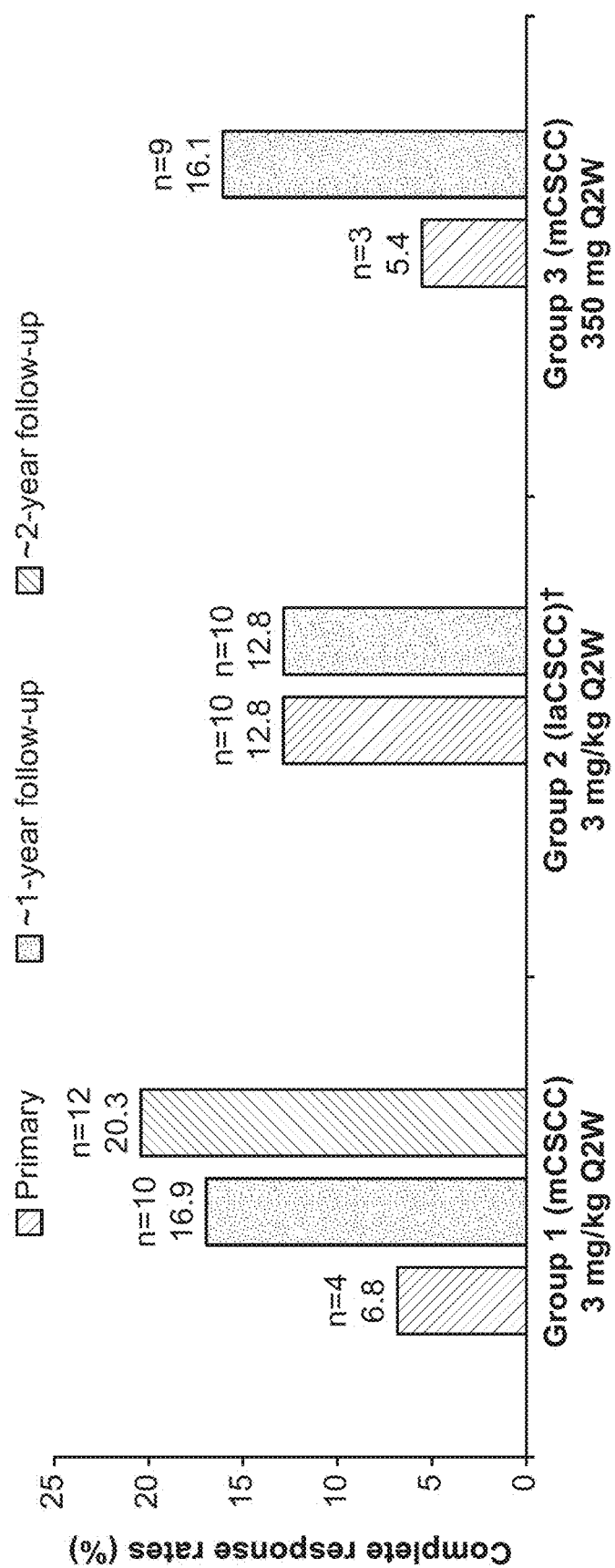
FIG. 11 is a graph showing CR rates over time compared to primary analyses, as described in Example 3. At the time of the Group 1 primary analysis, a pre-specified Group 2 interim analysis was performed. Among the 23 IaCSCC patients included in this pre-specified interim analysis, there were no complete responses.

Overall, 89 of 193 patients had a response to therapy, for an ORR of 46.1% (95% confidence interval [CI]: 38.9, 53.4); overall, 16.1% of patients achieved CR (see Example 1, Table 3). CR rates for this analysis were 20.3%, 12.8%, and 16.1% for Groups 1, 2, and 3, respectively. CR rates over time (compared to primary analyses) are presented in FIG. 11. Among 31 complete responders, median time to CR was 11.2 months (interquartile range: 7.4-14.8). ORR was 54.4% (95% CI: 47.1-61.6) for all patients; 50.8% (95% CI: 37.5-64.1) for Group 1, 56.4% (95% CI: 44.7-67.6) for Group 2, and 55.4% (95% CI: 41.5-68.7) for Group 3.

The CR rate for Group 1 increased from 6.8% in the primary analysis to 16.9% in the first follow-up analysis and to 20.3% at this subsequent follow-up analysis. For Group 2, there were no CRs at the interim analysis, but the CR rate was 12.8% at the primary analysis and is unchanged at this follow-up analysis. For Group 3, the CR rate increased from 5.4% at the primary analysis to 16.1% at this follow-up analysis. The median time to CR was 11.2 months.

Figure 12A:
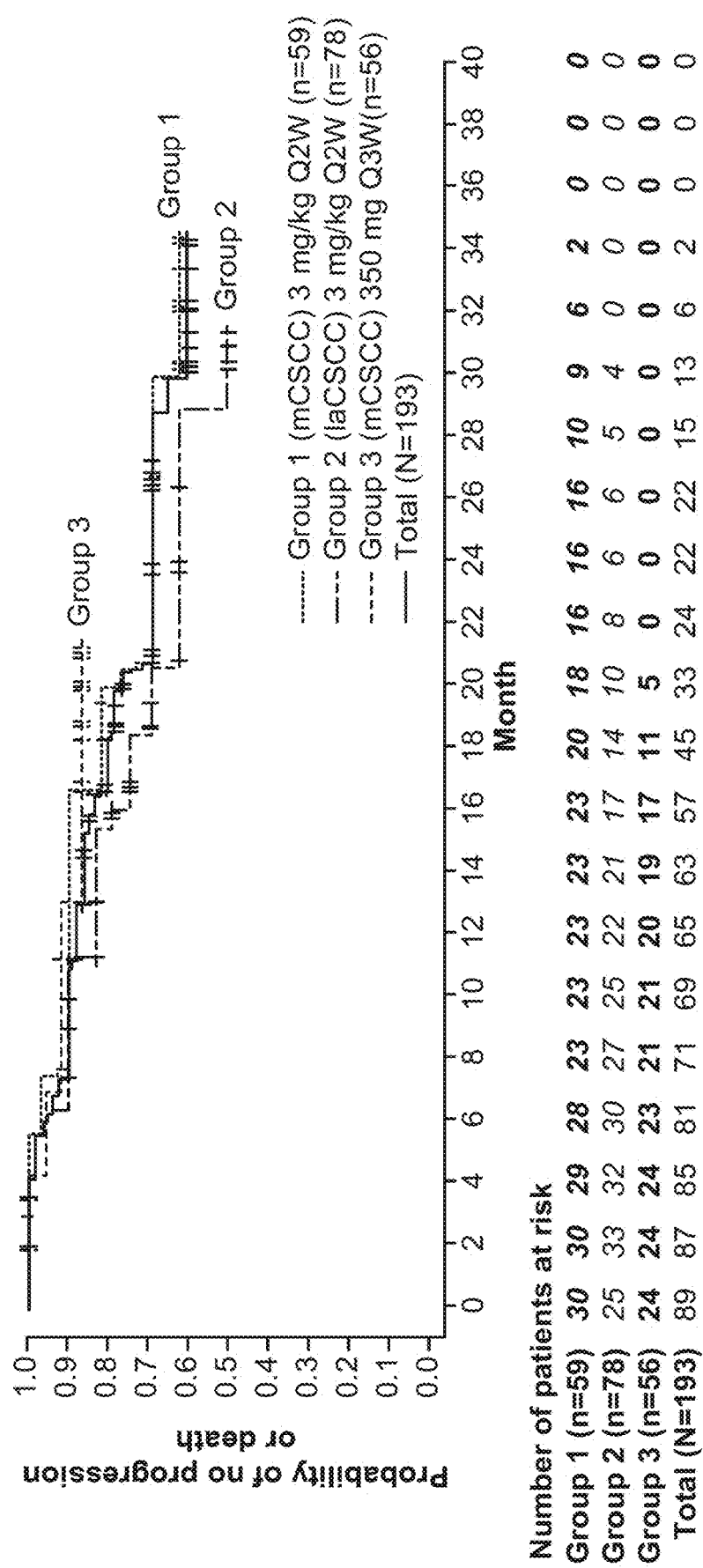
FIG. 12A shows KM curves for duration of response (DOR) of patients included in the study described in Example 3.
Figure 12B:
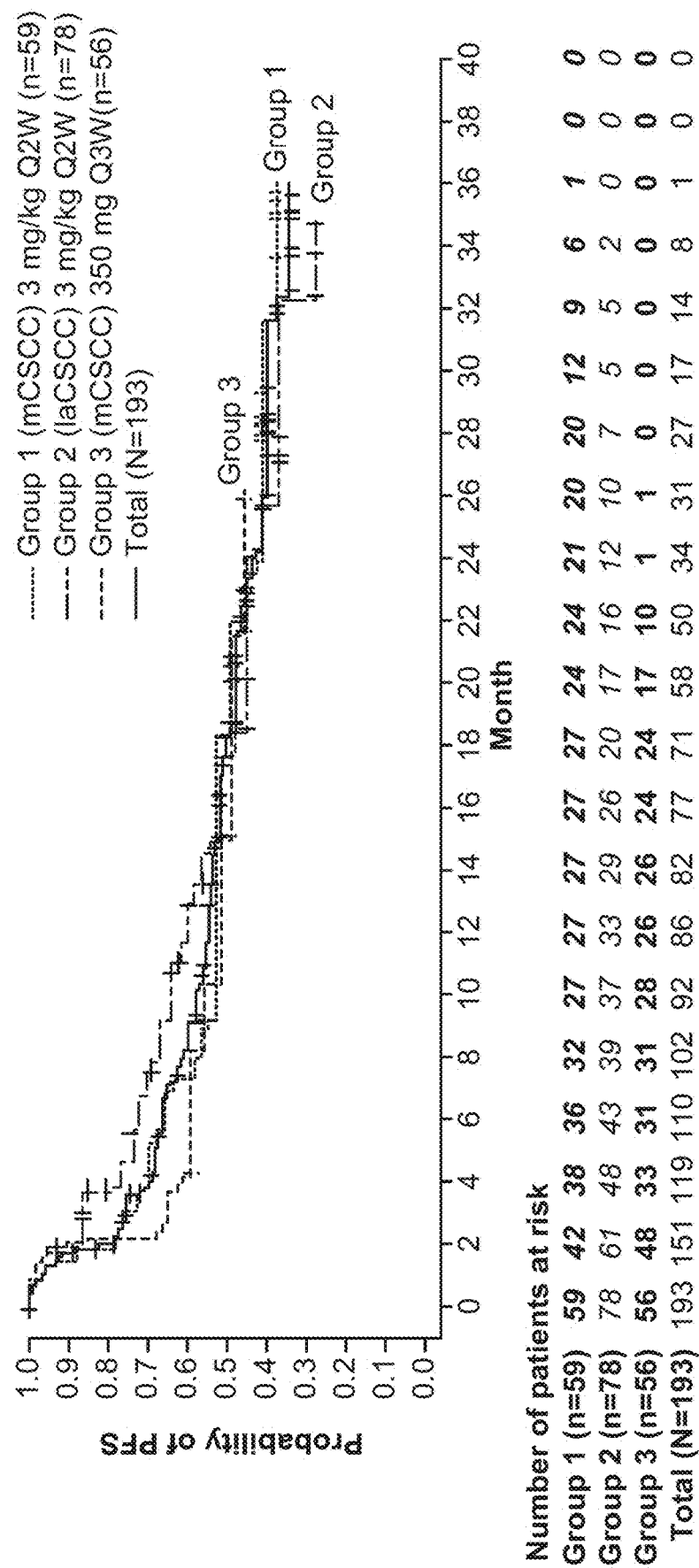
FIG. 12B shows KM curves for progression free survival (PFS) of patients included in the study described in Example 3.
Figure 12C:
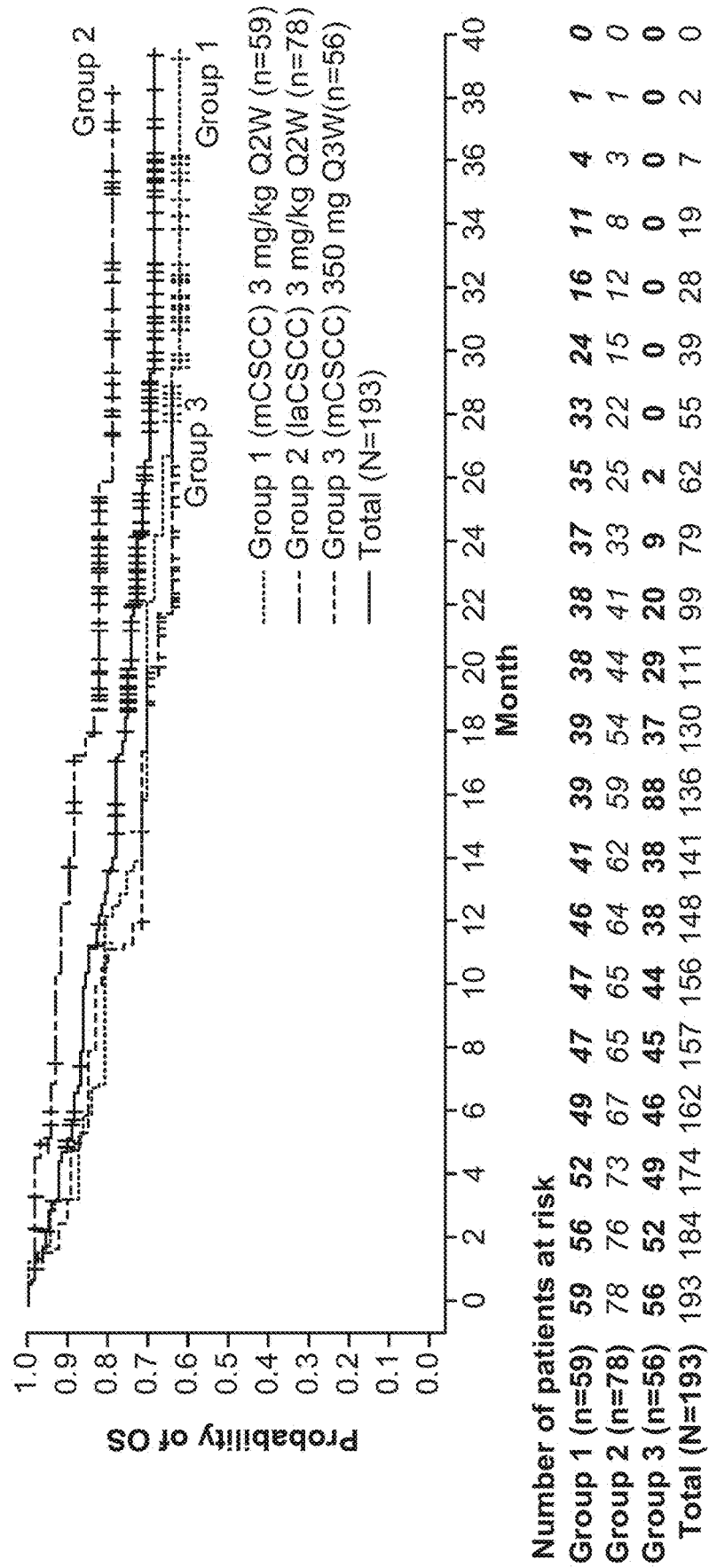
FIG. 12C shows KM curves for overall survival (OS) of patients included in the study described in Example 3.

DCR, durable DCR, median DOR, and KM 12-month estimate of DOR per ICR are provided in Example 1, Table 3. With 1-year additional follow-up, median DOR was not reached (observed DOR range: 1.9-34.3 months). In responding patients, the estimated proportion of patients with ongoing response at 12 months was 87.8% (95% CI: 78.5-93.3) (FIG. 12A). Estimated median PFS was 18.4 months (95% CI: 10.3-24.3) for all patients. The KM estimated progression-free probability at 24 months was 44.2% (95% CI: 36.1-52.1) (FIG. 12B). The KM estimated probability of OS at 24 months was 73.3% (95% CI: 66.1-79.2) (FIG. 12C). Median OS has not been reached.

Figure 13A:
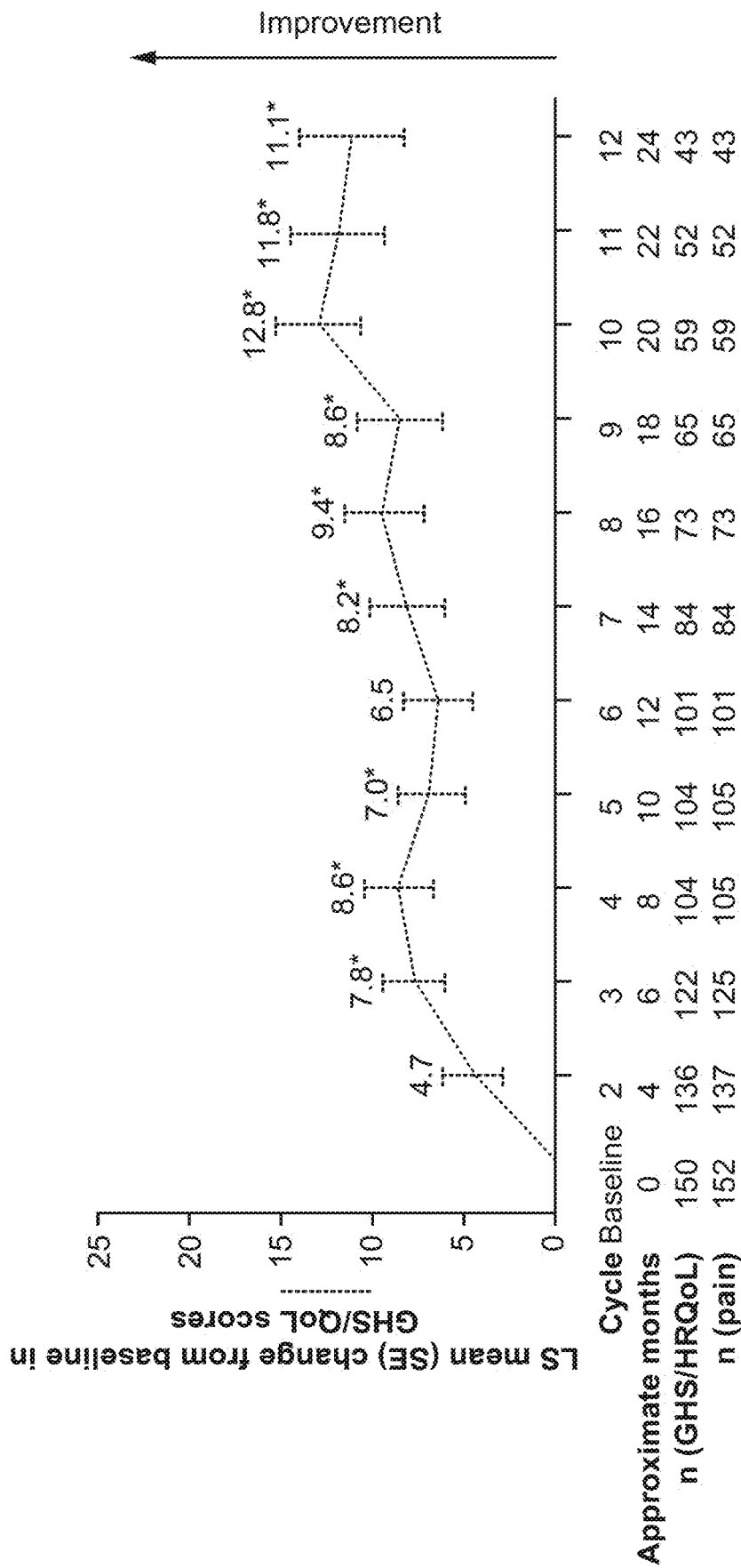
FIG. 13A is a graph showing change from baseline in Global Health Status/Quality of Life scores for patients included in the study described in Example 3.

Quality of life: Baseline scores for QLQ-C30 indicated generally moderate-to-high levels of functioning and moderate-to-low symptom burden (Table 5). For GHS/QoL, improvements were observed from cycle 2, with statistically significant improvement from baseline observed at cycle 3 (least squares (LS) mean [standard error (SE)] change 7.8 [1.6]; p<0.0001). Improvements in GHS/QoL had reached the clinically meaningful threshold (≥10-point change) by cycle 12 (LS mean [SE] change 11.1 [2.6]; p<0.0001) (FIG. 13A). Among functioning scales, significant improvements were observed in emotional functioning and social functioning scales at cycle 3 and cycle 12 (Table 5). Physical functioning, role functioning, and cognitive functioning did not deteriorate and remained stable relative to baseline (Table 5). Regarding symptoms, significant improvements from baseline were also observed for symptoms of nausea, pain, insomnia, appetite loss, and constipation by cycle 3 (Table 5), and as early as cycle 2 for pain (FIG. 13A). These symptoms had all reached the clinically meaningful threshold (≥10 points change) by cycle 12 (Table 5). Across all functioning scales and symptom scales, the proportion of patients with clinically meaningful deterioration was generally low at both cycle 3 and cycle 12.

TABLE 5

| | | LS mean change ± SE (n) | |
|---|---|---|---|
| QLQ-C30 scale/item | Baseline, mean ± SD (n) | Cycle 3 | Cycle 12 |
| Global Health Status/HRQOL | 65.1 ± 22.9 (150) | 7.8 ± 1.6 (122)** | 11.1 ± 2.6 (43)** |
| Functioning scales† | | | |
| Physical function | 80.1 ± 22.8 (151) | 1.1 ± 1.3 (124) | 4.0 ± 2.1 (43) |
| Role function | 75.8 ± 30.0 (151) | 0.4 ± 2.1 (123) | 5.6 ± 3.4 (43) |
| Emotional function | 80.2 ± 21.2 (151) | 4.2 ± 1.3 (123)* | 5.3 ± 2.2 (43)* |
| Cognitive function | 83.4 ± 22.2 (151) | 1.7 ± 1.4 (123) | 2.5 ± 2.3 (43) |
| Social function | 74.4 ± 31.8 (150) | 5.3 ± 1.8 (122)* | 8.6 ± 3.0 (43)* |
| Symptoms‡ | | | |
| Fatigue | 30.2 ± 24.6 (152) | −2.8 ± 1.7 (125) | −4.8 ± 2.8 (43) |
| Nausea/vomiting | 4.6 ± 12.2 (152) | −1.6 ± 0.8 (125)* | −2.9 ± 1.3 (43)* |
| Pain | 29.8 ± 30.4 (152) | −11.5 ± 1.9 (125)** | −14.3 ± 3.1 (43)** |
| Dyspnea | 12.9 ± 23.4 (152) | 0.7 ± 1.7 (125) | 1.5 ± 2.9 (43) |
| Insomnia | 27.4 ± 28.0 (151) | −9.1 ± 2.0 (123)** | −17.4 ± 3.3 (43)** |
| Appetite loss | 19.5 ± 29.3 (152) | −8.4 ± 1.6 (124)** | −13.7 ± 2.7 (43)** |
| Constipation | 13.6 ± 24.1 (152) | −4.5 ± 1.5 (125)* | −11.2 ± 2.5 (43)** |
| Diarrhea | 4.9 ± 13.6 (150) | 3.6 ± 1.4 (121)* | 0.6 ± 2.3 (43) |
| Financial difficulty | 19.1 ± 30.7 (150) | 0.5 ± 2.0 (122) | −3.4 ± 3.3 (43) |

*p < 0.05 and **p < 0.001 versus baseline.
†Higher scores reflect better outcomes.
‡Lower scores reflect better outcomes.

The questionnaire was administered on day 1 of each treatment cycle (treatment cycle defined as 8 weeks for Groups 1 and 2 and 9 weeks for Group 3).

HRQoL, health-related quality of life; LS, least squares; MMRM, mixed-effects repeated measures models; QLQ-C30, European Organisation for Research and Treatment of Cancer Core Quality of Life Questionnaire; SD, standard deviation; SE, standard error.

Figure 13B:
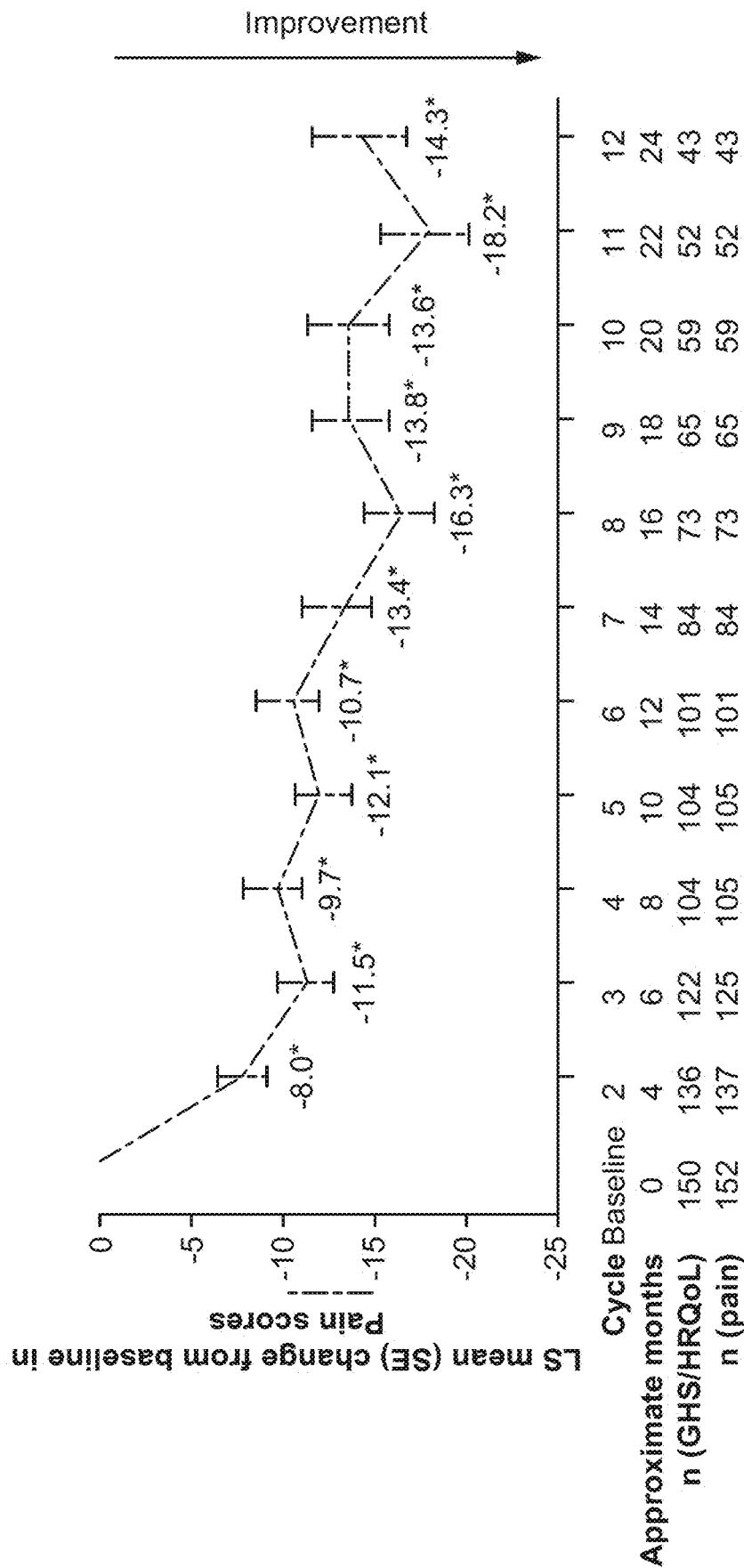
FIG. 13B is a graph showing change from baseline in Pain scores for patients included in the study described in Example 3. *p<0.0001. An increase of ≥10 points from baseline is considered a clinically meaningful improvement, while a decrease of ≥10 points from baseline is considered a clinically meaningful deterioration. Data are shown for day 1 of each cycle. The questionnaire was administered on day 1 of each treatment cycle (treatment cycle defined as 8 weeks for Groups 1 and 2 and 9 weeks for Group 3). Equivalent months are shown.

Early onset and durability of pain control: The KM estimate of median time (95% CI) to first clinically meaningful improvement for pain was 2.1 (2.0-3.7) months overall. The KM estimate of median time (95% CI) to first clinically meaningful deterioration for pain was 14.8 (9.2—not evaluable [NE]) months overall. LS mean (SE) change from baseline in pain score was −11.5 (1.9) at cycle 3, and −14.3 (3.1) at cycle 12 (FIG. 13B). LS mean change (SE) from baseline in pain score at first tumor response was −15.2 (1.5) in patients with objective response and −3.86 (2.1) in patients without objective response. The difference in LS mean change (95% CI) from baseline for pain score for responders versus non-responders was −11.3 (−16.3 to −6.3; p<0.0001). Among patients with objective response, the KM estimate of median time (95% CI) to first clinically meaningful improvement for pain was 2.1 (1.9-2.1) months and the KM estimate of median time (95% CI) to first clinically meaningful worsening for pain was 20.6 (9.2-NE) months.

Figure 14:
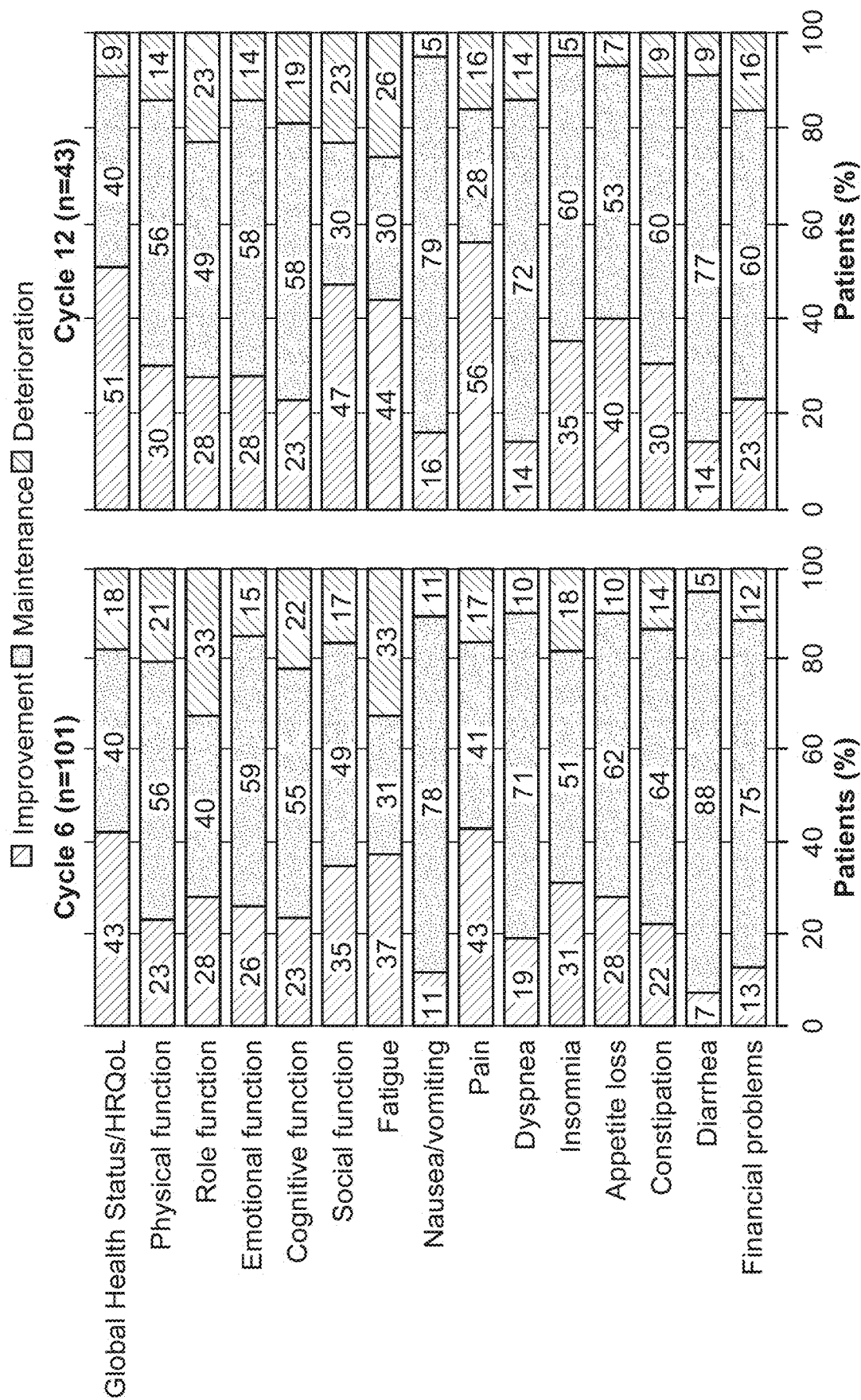
FIG. 14 shows the proportion of responding patients reporting clinically meaningful change (≥10-point change) at cycle 6 and cycle 12, as described in Example 3. The questionnaire was administered on day 1 of each treatment cycle (treatment cycle defined as 8 weeks for Groups 1 and 2 and 9 weeks for Group 3).

A substantial fraction of patients benefitted from treatment. Among all patients reporting clinically meaningful change (≥10-point change) by cycle 6, most patients experienced clinically meaningful improvements or stability in GHS/QoL (83%), functioning scales (68-85%), and symptoms (68-95%) (FIG. 14). Overall, 91% of responders experienced clinically meaningful improvement or stability in GHS/QoL scores at cycle 12, and most patients showed sustained improvement and stabilization across all functioning scales (77-86%) and symptoms (74-95%) by cycle 12 (FIG. 14). The proportions of patients with clinically meaningful deterioration in functioning scales were generally low at both evaluated time points (FIG. 14).

Safety: In total, 192 (99.5%) patients experienced at least one TEAE of any grade regardless of attribution. TEAEs leading to discontinuation were low (any grade: n=19, 9.8%; Grade ≥3: n=14, 7.3%). The most common TEAEs (all grades) were fatigue (n=67, 34.7%), diarrhea (n=53, 27.5%), and nausea (n=46, 23.8%). Overall, 94 (48.7%) patients experienced at least one Grade 3 TEAE regardless of attribution. The most common Grade ≥3 TEAEs were hypertension (n=9; 4.7%), anemia, and cellulitis (each n=8; 4.1%). No new TEAEs or treatment-related adverse events (TRAEs) resulting in death were reported for any group in this longer-term follow-up, compared to previous reports. Grade ≥3 TRAEs were reported in 33 (17.1%) patients; the most common were pneumonitis (n=5, 2.6%), autoimmune hepatitis (n=3; 1.6%), anemia, colitis, and diarrhea (all n=2; 1.0%). In total, 57 patients (29.5%) experienced at least one immune-related adverse event (irAE) of any grade, and 18 patients (9.3%) experienced at least one Grade ≥3 irAE. The most common Grade ≥3 irAEs were pneumonitis (n=5, 2.6%), autoimmune hepatitis (n=2, 1.0%), and diarrhea (n=2, 1.0%).

Discussion

The pooled analysis presented here demonstrates durability of responses to cemiplimab in CSCC, increasing CR rates over time, and confirms the substantial antitumor activity of cemiplimab in patients with advanced CSCC. An estimated 87.8% of responders had not progressed at 12 months. With median DOR not reached after an additional year of follow-up, the present analysis reinforces the activity of cemiplimab in a patient population that previously had no widely accepted standard of care. Furthermore, DOR and OS are longer than what has been previously described with other agents (Osoba et al., 1998). Additionally, this analysis demonstrates that cemiplimab treatment improves GHS/QoL and pain scores.

Pain is a key issue for patients with advanced CSCC, especially those with unresectable disease (Mills et al., 2012). The mean (standard deviation) baseline pain score of patients with advanced CSCC receiving cemiplimab of 29.8 (30.4) was significantly worse than reported by patients with advanced head and neck cancer (24.9 [26.3]; p<0.05; n=1, 722) and the general population (20.9 [27.6]; p<0.0001; n=7,802) (Scott et al., 2008). Here, the clinical responses observed correlated well with pain improvement, which positively impacted patient QoL. Cemiplimab resulted in pain reduction by cycle 2, with clinically meaningful reduction (≥10 points) from cycle 3, maintained through to cycle 12. The KM estimate of median time (95% CI) to first clinically meaningful improvement for pain was 2.1 months overall, and this was sustained to 14.8 months, demonstrating durability of pain control with cemiplimab. GHS/QoL improvement was observed as early as cycle 3, with clinically meaningful improvement seen by cycle 12. By cycle 6, most patients experienced clinically meaningful improvement or stability in GHS/QoL and functioning status, while maintaining low symptom burden.

There were no new safety signals or types of toxicities observed for cemiplimab.

This analysis confirms the substantial clinical activity of cemiplimab, including findings of improved CR rates over time compared to primary analyses, and an impressive and increasing DOR based on KM estimate at key landmarks in patients with advanced CSCC. Additionally, cemiplimab treatment resulted in clinically meaningful reduction in pain as early as cycle 2, maintained to cycle 12. Further, clinical response to cemiplimab was associated with reduction in pain. Most patients experienced clinically meaningful improvements or maintenance in GHS/QoL, functioning, and symptoms.

REFERENCES

1. Aaronson et al., *J Natl Cancer Inst*, 1993; 85:365-376.
2. Ahmed et al., *Expert Rev Clin Pharmacol*, 2019; 12:947-951.
3. Arunachalam et al., *Indian J Palliat Care.* 2011; 17:184-90.
4. Atherton et al., *Support Care Cancer*, 2012 August; 20(8):1729-1735.
5. Bottomley et al., *Eur J Cancer*, 2005; 41(12):1697-709.
6. Brook et al., *Radiat Oncol J.* 2020; 38:84-92.
7. Burova et al., *Mol Cancer Ther.* 2017; 16:861-70.
8. Chren et al., *J Cutan Med Surg.*, 2001; 5:105-110.
9. Cowey et al., *Cancer Med.* 2020; 9:7381-7.
10. Cranmer et al., *Oncologist.* 2010; 15:1320-8.
11. Eisenhauer et al., *Eur J Cancer*, 2009; 45:228-247.
12. Gerring et al., *Eye (Lond).* 2017; 31:379-88.
13. Grob et al., *J Clin Oncol.* 2020; 38:2916-25.
14. Hansson et al., *Eur J Dermatol.,* 2018; 28:775-783.
15. Katz et al., *Head Neck.* 2003; 25:103-12.
16. Karia et al., *J Clin Oncol.* 2014; 32:327-34.
17. Kondo et al., *Ophthalmic Plast Reconstr Surg.* 2013; 29:51-6.

18. LIBTAYO® [cemiplimab-rwlc] injection full US prescribing information, Regeneron Pharmaceuticals, Inc. and Sanofi-Aventis US LLC (March 2020).
19. Maubec et al., *J Clin Oncol.* 2020; 38:3051-61.
20. McLeod et al., *Expert Rev Pharmacoecon Outcomes Res,* 2011; 11:163-69.
21. Migden et al., *Cancer Treat Rev.,* 2018; 64:1-10.
22. Migden et al., *N Engl J Med,* 2018; 379:341-351.
23. Migden et al., *J Clin Oncol,* 2019; 37(15 suppl):6015.
24. Migden et al., *Lancet Oncol,* 2020; 21:294-305.
25. Migden et al., *J Clin Oncol,* May 2020, 38, no. 15 suppl; abstr 10033.
26. Mills et al., *Arch Dermatol,* 2012; 148:1422-1423.
27. National Comprehensive Cancer Network. National Comprehensive Cancer Network Clinical practice guidelines in oncology: squamous cell skin cancer (Version 2.2020) at [https://www.nccn.org/professionals/physician_gls/pdf/squamous.pdf], 2020
28. National Institute for Health and Care Excellence. Cemiplimab for treating metastatic or locally advanced cutaneous squamous cell carcinoma at [https://www.nice.org.uk/guidance/gid-ta10304/documents/final-appraisal-determination-document], 2019
29. Osoba et al., *J Clin Oncol,* 1998; 16:139-144.
30. Que et al., *J Am Acad Dermatol,* 2018; 78:237-47.
31. Revicki et al., *J Clin Epidemiol,* 2008; 61:102-109.
32. Rhee et al., *Laryngoscope.* 2005; 115:1178-85.
33. Rischin et al., *Ann Oncol,* 2019; 30(suppl 5):536-537.
34. Rischin et al., *J Immunother Cancer.* 2020; 8:e000775.
35. Schmults et al., *JAMA Dermatol.* 2013; 149:541-7.
36. Scott et al., EORTC QLQ-C30. Brussels: EORTC; 2008.
37. Steenrod et al., *Dermatol Ther (Heidelb).,* 2015; 5:183-199.
38. Stratigos et al., *Eur J Cancer.* 2015; 51:1989-2007.
39. Stratigos et al., *Eur J Cancer.* 2020; 128:60-82.
40. Stratigos et al., *Ann Oncol.,* 2020; 31(suppl 4):S1175-1176.
41. Wang et al., *JAMA Oncol.* 2019; 5:1008-19.
42. Weinberg et al., *Dermatol Surg.* 2007; 33:885-99.
43. Yet et al., *PloS One.* 2015; 10:e0136460-e.

The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating or inhibiting cancer pain, comprising:

(a) selecting a patient with cutaneous squamous cell carcinoma (CSCC), wherein the patient is receiving analgesic therapy as a background medication; and (b) administering to the patient a therapeutically effective amount of a programmed death 1 (PD-1) inhibitor, wherein the PD-1 inhibitor is an anti-PD-1 antibody or antigen-binding fragment thereof that comprises a heavy chain variable region (HCVR) comprising three heavy chain complementarity determining regions (CDRs) (HCDR1, HCDR2 and HCDR3) and a light chain variable region (LCVR) comprising three light chain CDRs (LCDR1, LCDR2 and LCDR3), wherein: HCDR1 has an amino acid sequence of SEQ ID NO: 3; HCDR2 has an amino acid sequence of SEQ ID NO: 4; HCDR3 has an amino acid sequence of SEQ ID NO: 5; LCDR1 has an amino acid sequence of SEQ ID NO: 6; LCDR2 has an amino acid sequence of SEQ ID NO: 7; and LCDR3 has an amino acid sequence of SEQ ID NO: 8;

wherein the patient's use of analgesic therapy after the administration of the PD-1 inhibitor is reduced.

2. The method of claim 1, wherein the CSCC is metastatic CSCC or unresectable locally advanced CSCC.

3. The method of claim 1, wherein functioning and quality of life of the patient is improved or maintained from baseline, as measured by EORTC QLQ-C30 and SKIN-DEX-16.

4. The method of claim 1, wherein the analgesic therapy is selected from an opioid, a non-steroid anti-inflammatory drug (NSAID), a steroid, acetaminophen, and combinations thereof.

5. The method of claim 1, wherein the analgesic therapy comprises an opioid.

6. The method of claim 1, further comprising reducing the amount of the analgesic therapy received by the patient by 20% or more within 1 year after administration of the PD-1 inhibitor.

7. The method of claim 1, wherein the pain is reduced by about 20% or more within 1 year after administration of the PD-1 inhibitor.

8. The method of claim 1, wherein the administration of the PD-1 inhibitor concurrently leads to reduced cancer pain and at least 30% decrease in tumor cells or tumor size.

9. The method of claim 1, wherein the administration of the PD-1 inhibitor concurrently leads to reduced analgesic use and at least 30% decrease in tumor cells or tumor size.

10. The method of claim 1, wherein the administration of the PD-1 inhibitor concurrently leads to reduced opioid use and at least 30% decrease in tumor cells or tumor size.

11. The method of claim 1, wherein the administration of the PD-1 inhibitor further reduces pain, promotes tumor regression, reduces tumor cell load, reduces tumor burden, prevents tumor recurrence in the patient, and/or increases patient survival.

12. The method of claim 1, wherein the PD-1 inhibitor is administered in combination with an additional therapeutic agent or therapy selected from an analgesic, a non-steroid anti-inflammatory drug (NSAID), radiation, surgery, a cancer vaccine, imiquimod, an anti-viral agent, photodynamic therapy, HHI therapy, a PD-L1 inhibitor, a LAG3 inhibitor, a CTLA-4 inhibitor, a GITR agonist, a TIM3 inhibitor, a BTLA inhibitor, a TIGIT inhibitor, a CD38 inhibitor, a CD47 inhibitor, an IDO inhibitor, a CD28 activator, a VEGF antagonist, an Ang2 inhibitor, a TGFβ inhibitor, an EGFR inhibitor, an antibody to a tumor-specific antigen, a GM-CSF, an oncolytic virus, a cytotoxin, a chemotherapeutic agent, an IL-6R inhibitor, an IL-4R inhibitor, an IL-10 inhibitor, a cytokine, an antibody drug conjugate, an anti-inflammatory drug, and a dietary supplement.

13. The method of claim 1, wherein the HCVR comprises an amino acid sequence of SEQ ID NO: 1.

14. The method of claim 1, wherein the LCVR comprises an amino acid sequence of SEQ ID NO: 2.

15. The method of claim 1, wherein the anti-PD-1 antibody or antigen-binding fragment thereof comprises an HCVR/LCVR amino acid sequence pair of SEQ ID NOs: 1/2.

16. The method of claim 1, wherein the anti-PD-1 antibody comprises a heavy chain and a light chain, wherein the heavy chain has an amino acid sequence of SEQ ID NO: 9.

17. The method of claim 1, wherein the anti-PD-1 antibody comprises a heavy chain and a light chain, wherein the light chain has an amino acid sequence of SEQ ID NO: 10.

18. The method of claim 1, wherein the anti-PD-1 antibody comprises a heavy chain and a light chain, wherein the heavy chain has an amino acid sequence of SEQ ID NO: 9 and the light chain has an amino acid sequence of SEQ ID NO: 10.

19. The method of claim 1, wherein the PD-1 inhibitor is an anti-PD-1 antibody or antigen-binding fragment thereof comprising a HCVR with 90%, 95%, 97% or 98% sequence identity to SEQ ID NO: 1.

20. The method of claim 1, wherein the PD-1 inhibitor is an anti-PD-1 antibody or antigen-binding fragment thereof comprising a LCVR with 90%, 95%, 97% or 98% sequence identity to SEQ ID NO: 2.

21. The method of claim 1, wherein the PD-1 inhibitor is an anti-PD-1 antibody or antigen-binding fragment thereof comprising a HCVR with 90%, 95%, 97% or 98% sequence identity to SEQ ID NO: 1, and a LCVR with 90%, 95%, 97% or 98% sequence identity to SEQ ID NO: 2.

22. The method of claim 1, wherein the PD-1 inhibitor is cemiplimab or a bioequivalent thereof.

23. The method of claim 1, wherein the PD-1 inhibitor is cemiplimab.

24. The method of claim 1, wherein the PD-1 inhibitor is administered at a dose of 5 mg to 1500 mg.

25. The method of claim 1, wherein the PD-1 inhibitor is administered at a dose of 200 mg, 250 mg, or 350 mg.

26. The method of claim 1, wherein the PD-1 inhibitor is administered at a dose of 1 mg/kg to 20 mg/kg of the patient's body weight.

27. The method of claim 1, wherein the PD-1 inhibitor is administered at a dose of 1 mg/kg, 3 mg/kg or 10 mg/kg of the patient's body weight.

28. The method of claim 1, wherein the PD-1 inhibitor is administered as one or more doses, wherein each dose is administered every two weeks, three weeks, four weeks, five weeks or six weeks.

29. The method of claim 1, wherein the PD-1 inhibitor is administered intravenously or subcutaneously.

30. A method of reducing use of analgesic therapy by a cancer patient, comprising:
(a) selecting a patient with cutaneous squamous cell carcinoma (CSCC wherein the patient is receiving analgesic therapy as a background medication prior to the administration of a programmed death 1 (PD-1) inhibitor; and
(b) administering to the patient a therapeutically effective amount of a PD-1 inhibitor, wherein the PD-1 inhibitor is an anti-PD-1 antibody or antigen-binding fragment thereof that comprises a heavy chain variable region (HCVR) comprising three heavy chain complementarity determining regions (CDRs) (HCDR1, HCDR2 and HCDR3) and a light chain variable region (LCVR) comprising three light chain CDRs (LCDR1, LCDR2 and LCDR3), wherein: HCDR1 has an amino acid sequence of SEQ ID NO: 3; HCDR2 has an amino acid sequence of SEQ ID NO: 4; HCDR3 has an amino acid sequence of SEQ ID NO: 5; LCDR1 has an amino acid sequence of SEQ ID NO: 6; LCDR2 has an amino acid sequence of SEQ ID NO: 7; and LCDR3 has an amino acid sequence of SEQ ID NO: 8;

wherein the patient's use of analgesic therapy after the administration of the PD-1 inhibitor is reduced.

31. The method of claim 30, wherein the CSCC is metastatic CSCC or unresectable locally advanced CSCC.

32. The method of claim 30, wherein the analgesic therapy is selected from an opioid, a non-steroid anti-inflammatory drug (NSAID), a steroid, acetaminophen, and combinations thereof.

33. The method of claim 30, wherein the analgesic therapy comprises an opioid.

34. The method of claim 30, wherein the amount of analgesic therapy received by the patient is reduced by at least 20% within 1 year after administration of the PD-1 inhibitor as compared to the amount of analgesic therapy received by the patient before administration of the PD-1 inhibitor.

35. The method of claim 30, wherein the administration of the PD-1 inhibitor concurrently leads to reduced analgesic use and at least 30% decrease in tumor cells or tumor size.

36. The method of claim 30, wherein the administration of the PD-1 inhibitor concurrently leads to reduced opioid use and at least 30% decrease in tumor cells or tumor size.

37. The method of claim 30, wherein the administration of the PD-1 inhibitor concurrently leads to reduced cancer pain and at least 30% decrease in tumor cells or tumor size.

38. The method of claim 30, wherein the administration of the PD-1 inhibitor concurrently leads to reduced cancer pain, reduced opioid use, and a tumor response selected from the group consisting of stable disease (SD), partial response (PR) and complete response (CR), as determined using RECIST criteria.

39. The method of claim 30, wherein the PD-1 inhibitor is administered in combination with an additional therapeutic agent or therapy selected from an analgesic, a non-steroid anti-inflammatory drug (NSAID), radiation, surgery, a cancer vaccine, imiquimod, an anti-viral agent, photodynamic therapy, HHI therapy, a PD-L1 inhibitor, a LAG3 inhibitor, a CTLA-4 inhibitor, a GITR agonist, a TIM3 inhibitor, a BTLA inhibitor, a TIGIT inhibitor, a CD40 inhibitor, a CD47 inhibitor, an IDO inhibitor, a CD28 activator, a VEGF antagonist, an Ang2 inhibitor, a TGFβ inhibitor, an EGFR inhibitor, an antibody to a tumor-specific antigen, a GM-CSF, an oncolytic virus, a cytotoxin, a chemotherapeutic agent, an IL-6R inhibitor, an IL-4R inhibitor, an IL-10 inhibitor, a cytokine, an antibody drug conjugate, an anti-inflammatory drug, and a dietary supplement.

40. The method of claim 30, wherein the PD-1 inhibitor is administered at a dose of 5 mg to 1500 mg.

41. The method of claim 30, wherein the PD-1 inhibitor is administered at a dose of 200 mg, 250 mg, or 350 mg.

42. The method of claim 30, wherein the PD-1 inhibitor is administered at a dose of 1 mg/kg to 20 mg/kg of the patient's body weight.

43. The method of claim 30, wherein the PD-1 inhibitor is administered at a dose of 1 mg/kg, 3 mg/kg or 10 mg/kg of the patient's body weight.

44. The method of claim 30, wherein the PD-1 inhibitor is administered as one or more doses, wherein each dose is administered every two weeks, three weeks, four weeks, five weeks or six weeks.

45. The method of claim 30, wherein the PD-1 inhibitor is administered intravenously or subcutaneously.

* * * * *

SEQUENCE LISTING

```
<160> NUMBER OF SEQ ID NOS: 12

<210> SEQ ID NO 1
<211> LENGTH: 117
<212> TYPE: PRT
<213> ORGANISM: Artificial sequence
<220> FEATURE:
<223> OTHER INFORMATION: HCVR

<400> SEQUENCE: 1

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial sequence
<220> FEATURE:
<223> OTHER INFORMATION: LCVR

<400> SEQUENCE: 2

Asp Ile Gln Met Thr Gln Ser Pro Ser Ser Leu Ser Ala Ser Val Gly
1               5                   10                  15
```

```
Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Leu His Gly Gly Val Pro Ser Arg Phe Ser Gly
50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105

<210> SEQ ID NO 3
<211> LENGTH: 8
<212> TYPE: PRT
<213> ORGANISM: Artificial sequence
<220> FEATURE:
<223> OTHER INFORMATION: HCDR1

<400> SEQUENCE: 3

Gly Phe Thr Phe Ser Asn Phe Gly
1               5

<210> SEQ ID NO 4
<211> LENGTH: 8
<212> TYPE: PRT
<213> ORGANISM: Artificial sequence
<220> FEATURE:
<223> OTHER INFORMATION: HCDR2

<400> SEQUENCE: 4

Ile Ser Gly Gly Gly Arg Asp Thr
1               5

<210> SEQ ID NO 5
<211> LENGTH: 10
<212> TYPE: PRT
<213> ORGANISM: Artificial sequence
<220> FEATURE:
<223> OTHER INFORMATION: HCDR3

<400> SEQUENCE: 5

Val Lys Trp Gly Asn Ile Tyr Phe Asp Tyr
1               5                   10

<210> SEQ ID NO 6
<211> LENGTH: 6
<212> TYPE: PRT
<213> ORGANISM: Artificial sequence
<220> FEATURE:
<223> OTHER INFORMATION: LCDR1

<400> SEQUENCE: 6

Leu Ser Ile Asn Thr Phe
1               5

<210> SEQ ID NO 7
<211> LENGTH: 3
<212> TYPE: PRT
<213> ORGANISM: Artificial sequence
<220> FEATURE:
<223> OTHER INFORMATION: LCDR2
```

<400> SEQUENCE: 7

Ala Ala Ser
1

<210> SEQ ID NO 8
<211> LENGTH: 9
<212> TYPE: PRT
<213> ORGANISM: Artificial sequence
<220> FEATURE:
<223> OTHER INFORMATION: LCDR3

<400> SEQUENCE: 8

Gln Gln Ser Ser Asn Thr Pro Phe Thr
1               5

<210> SEQ ID NO 9
<211> LENGTH: 444
<212> TYPE: PRT
<213> ORGANISM: Artificial sequence
<220> FEATURE:
<223> OTHER INFORMATION: HC 1-117; 118-444

<400> SEQUENCE: 9

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

```
Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 10
<211> LENGTH: 214
<212> TYPE: PRT
<213> ORGANISM: Artificial sequence
<220> FEATURE:
<223> OTHER INFORMATION: LC 1-108; 109-214

<400> SEQUENCE: 10

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
            210

<210> SEQ ID NO 11
<211> LENGTH: 120
<212> TYPE: PRT
<213> ORGANISM: Artificial sequence
<220> FEATURE:
<223> OTHER INFORMATION: HCVR

<400> SEQUENCE: 11

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Arg Gly Leu Glu Trp Val
            35                  40                  45

Ser Gly Ile His Trp His Gly Lys Arg Thr Gly Tyr Ala Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Lys Gly Glu Asp Thr Ala Leu Tyr His Cys
                85                  90                  95

Val Arg Gly Gly Met Ser Thr Gly Asp Trp Phe Asp Pro Trp Gly Gln
            100                 105                 110

Gly Thr Leu Val Ile Val Ser Ser
            115                 120

<210> SEQ ID NO 12
<211> LENGTH: 108
<212> TYPE: PRT
<213> ORGANISM: Artificial sequence
<220> FEATURE:
<223> OTHER INFORMATION: LCVR

<400> SEQUENCE: 12

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
            35                  40                  45

Tyr Val Ala Ser Ser Leu Gln Ser Gly Val Pro Ser Arg Phe Ser Gly
        50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```